United States Patent
Gaston et al.

(10) Patent No.: US 10,881,633 B2
(45) Date of Patent: *Jan. 5, 2021

(54) COMPOSITIONS AND METHODS FOR STIMULATING VENTILATORY AND/OR RESPIRATORY DRIVE

(71) Applicant: CASE WESTERN RESERVE UNIVERSITY, Cleveland, OH (US)

(72) Inventors: Benjamin Gaston, Cleveland, OH (US); Stephen Lewis, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/515,355

(22) Filed: Jul. 18, 2019

(65) Prior Publication Data

US 2019/0358189 A1   Nov. 28, 2019

Related U.S. Application Data

(63) Continuation-in-part of application No. 16/139,937, filed on Sep. 24, 2018, now Pat. No. 10,543,187, which is a continuation of application No. 15/543,524, filed as application No. PCT/US2016/013241 on Jan. 13, 2016, now Pat. No. 10,080,732.

(60) Provisional application No. 62/102,902, filed on Jan. 13, 2015.

(51) Int. Cl.
*A61K 31/225* (2006.01)
*A61K 45/06* (2006.01)
*A61K 9/00* (2006.01)

(52) U.S. Cl.
CPC .......... *A61K 31/225* (2013.01); *A61K 9/0019* (2013.01); *A61K 45/06* (2013.01)

(58) Field of Classification Search
CPC combination set(s) only.
See application file for complete search history.

(56) References Cited

U.S. PATENT DOCUMENTS

| | | | |
|---|---|---|---|
| 6,242,573 | B1 | 6/2001 | Goto et al. |
| 2002/0115723 | A1 | 8/2002 | Iwasaki et al. |
| 2013/0131028 | A1 | 5/2013 | Snyder et al. |
| 2013/0338225 | A1 | 12/2013 | Ward et al. |

FOREIGN PATENT DOCUMENTS

WO   1992/204024 A2   3/1992

OTHER PUBLICATIONS

Gupta et al, Feb. 2018 (https://www.apsf.org/newsletter/february-2018/).*
Mendoza et al. (Respir Physiol Neurobiol. (2013) 189(1): 136-143.

* cited by examiner

*Primary Examiner* — Shirley V Gembeh
(74) *Attorney, Agent, or Firm* — Tarolli, Sundheim, Covell & Tummino LLP

(57) ABSTRACT

A method of stimulating ventilatory and/or respiratory drive in a subject in need thereof includes administering to the subject a therapeutically effective amount of a composition comprising a D-cysteine alkyl ester, adduct thereof, or pharmaceutically acceptable salt, tautomer, or solvate thereof.

20 Claims, 25 Drawing Sheets

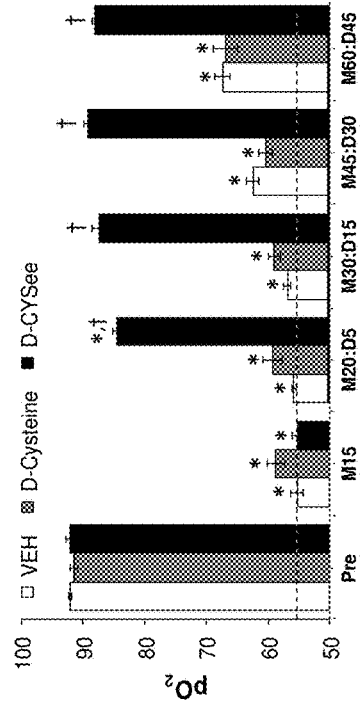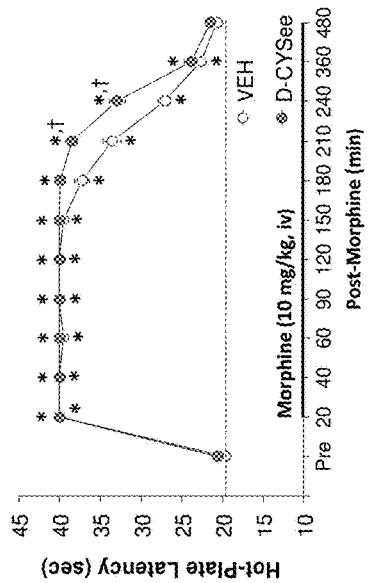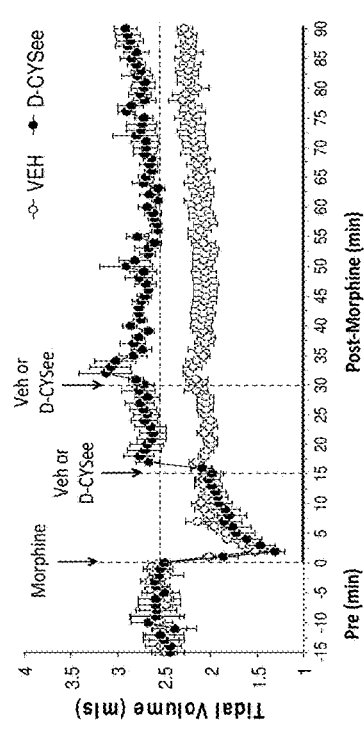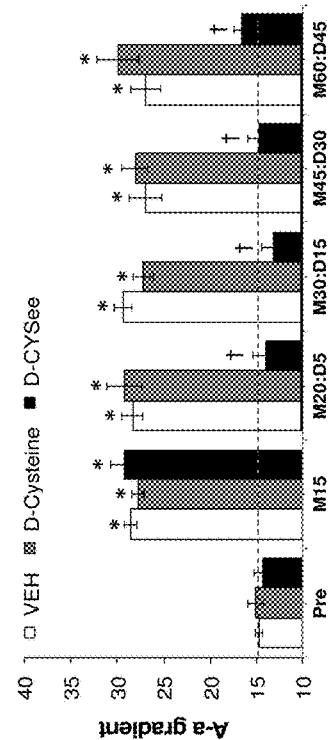
Fig. 1

D-CYSee reverses morphine-induced increases in A-a gradient

The Alveolar-arterial (A-a) gradient is a measure of the difference between alveolar (A) and the arterial (a) concentrations of oxygen. It is used to diagnose the source of hypoxemia and helps to assess the integrity of alveolar capillary unit. In conditions of ventilation perfusion mismatch, oxygen is not effectively transferred from the alveoli to the blood, which results in elevated A-a gradient. An elevated A-a gradient reflects increased ventilation-perfusion mismatch.

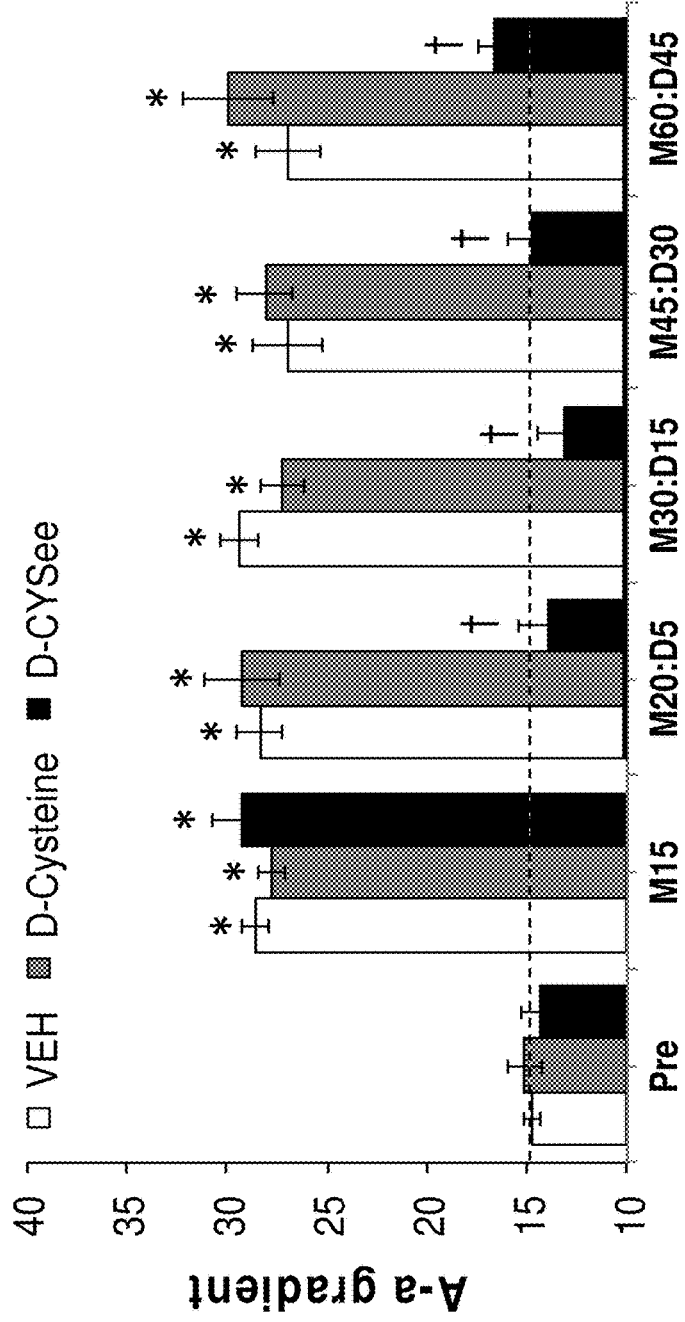

Fig. 15

D-CYSee slightly diminishes 5 mg/kg morphine-induced analgesia

Hot-Plate Latency (HPL) – time that a rat will lift/lick a paw upon placement on a thermal plate of 55°C in temperature D-CYSee (500 µmol/kg, iv) or vehicle (saline, iv) were injected to Sprague-Dawley rats and after 15 min, TFL was determined (Pre value). Immediately afterwards, all rats received a bolus injection of morphine (5 mg/kg, iv) and HFL monitored at regular times thereafter. A cut-off latency of 40 sec was chosen to limit heat injury. Data are expressed as HPL (sec) and %MPE [%Maximum Possible Effect = ((Morphine-induced HPL – pre-morphine HPL)/(Cut-off Latency-pre-drug latency))*100.

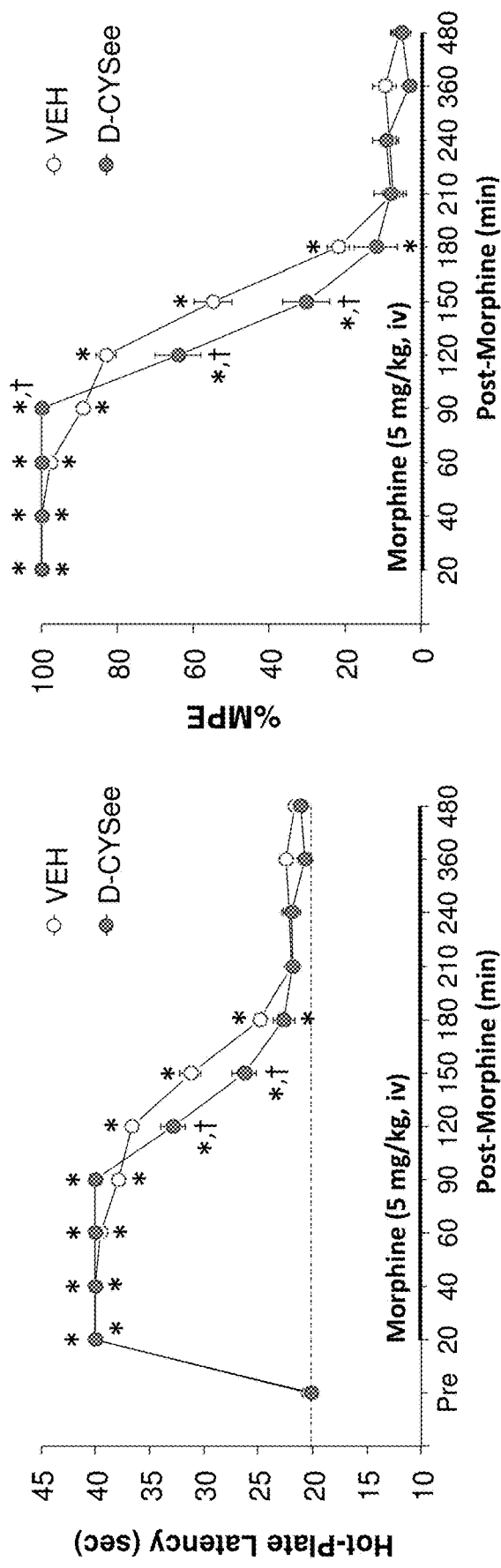

Fig. 18

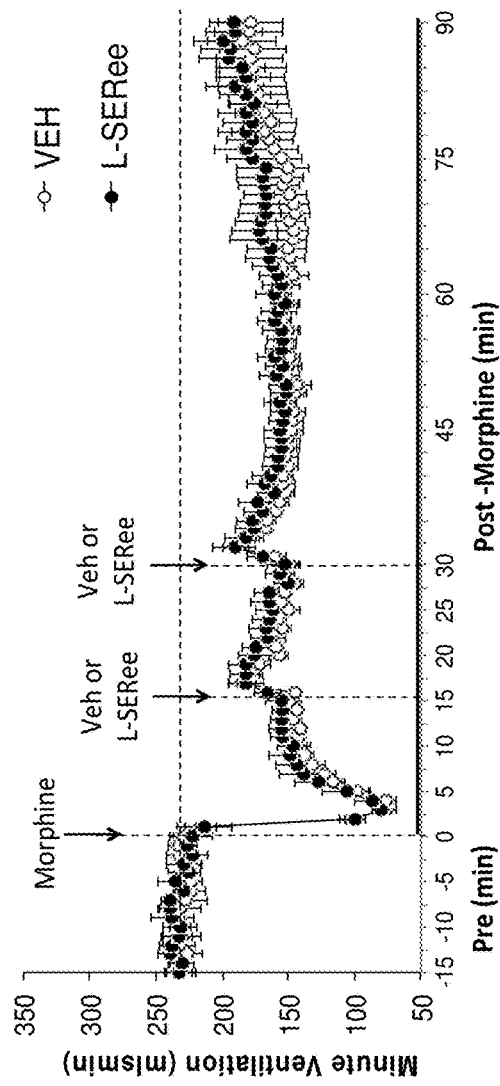
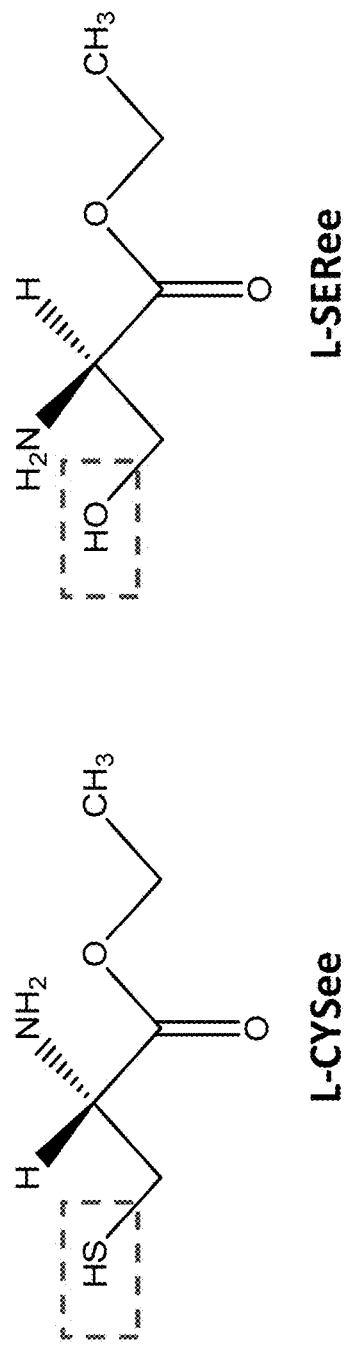
Fig. 21

N-acetyl-L-cysteine methylester (L-NACme) minimally affects the ventilatory effects of morphine
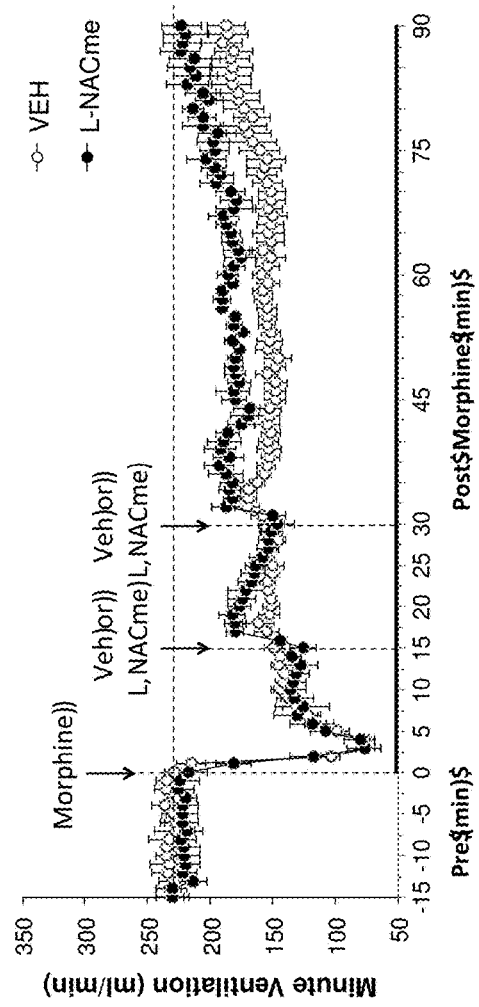
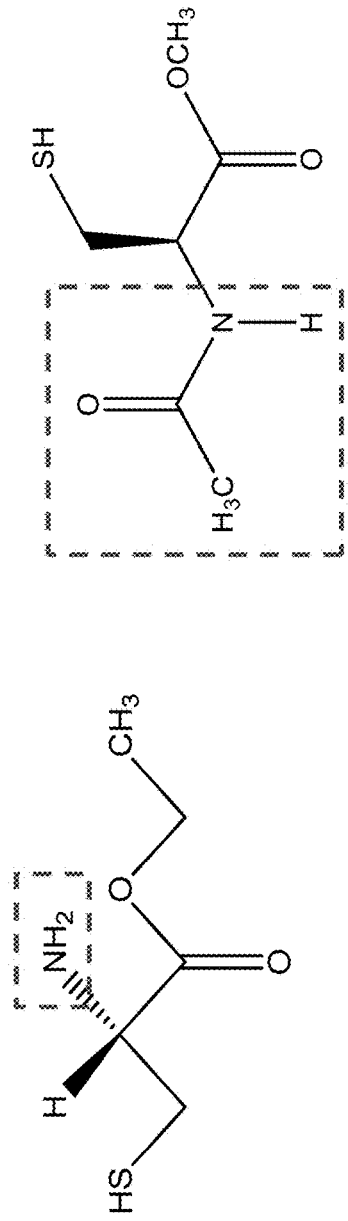
Substitutions on the amino moiety of cysteine impair activity
Fig. 22

COMPOSITIONS AND METHODS FOR STIMULATING VENTILATORY AND/OR RESPIRATORY DRIVE

RELATED APPLICATION

This application is a Continuation-in-Part of U.S. Ser. No. 16/139,937, filed Sep. 24, 2018, which is a Continuation of U.S. Ser. No. 15/543,527, filed Jul. 13, 2017, which is a National Phase Filing of PCT/US2016/013241, which is claims priority from U.S. Provisional Application Nos. 62/102,902, filed Jan. 13, 2016, the subject matter of which are incorporated herein by reference in their entirety.

TECHNICAL FIELD

Embodiments described herein relate to compositions and methods of stimulating ventilatory and/or respiratory drive in a subject in need thereof, and particularly relates to compositions and methods of treating breathing diseases and/or disorders associated with impaired ventilatory and/or respiratory drive.

BACKGROUND

Normal control of breathing is a complex process that involves the body's interpretation and response to chemical stimuli, such as carbon dioxide, pH and oxygen levels in blood, tissues and the brain. Breathing control is also affected by wakefulness (i.e., whether the patient is awake or sleeping). Within the brain medulla there are respiratory control centers that interpret the various signals that affect respiration and issue commands to muscles that perform the work of breathing. Key muscle groups are located in the abdomen, diaphragm, larynx, pharynx and thorax. Sensors located centrally and peripherally provide input to the brain's central respiration control areas that enable response to changing oxygen requirements.

Normal respiratory rhythm is maintained primarily by the body's rapid response to changes in carbon dioxide levels ($CO_2$). Increased $CO_2$ levels signal the body to increase breathing rate and depth resulting in higher oxygen levels and subsequent lower $CO_2$ levels. Conversely, low $CO_2$ levels can result in periods of apnea (no breathing) since the stimulation to breathe is absent. This is what happens when a person hyperventilates. Additionally, low blood oxygen levels stimulate respiratory drive, and this mechanism can become the primary driver in patients with chronically high $PCO_2$ levels.

Impaired ventilatory drive can complicate a broad spectrum of diseases in pulmonary, sleep, and critical care medicine. Patients with various forms of chronic obstructive pulmonary disease (COPD)—among which can be considered late-stage cystic fibrosis (CF)—can have impaired ventilatory responses when treated with oxygen or narcotics. In obstructive sleep apnea (OSA), intermittent hypoxia associated with impaired short- and long-term facilitation of hypoxic ventilatory drive and with loop gain may predispose to perioperative complications and adverse neurocognitive sequelae. A variety of other conditions with components of disordered ventilatory control—ranging from congestive heart failure (CHF) to Arnold-Chiari malformation—can only be managed with mechanical ventilation. Additionally, endotracheally-intubated patients in the critical care setting who require narcotics for pain control can become unmanageable if narcotic use is stopped, but can fail extubation because of respiratory depression if the narcotic is continued. These pulmonary and critical care issues can be all the more challenging in patients with underlying COPD, CF, CHF, OSA and other conditions affecting ventilatory drive.

Few medications are effective as respiratory stimulants. Methylxanthines can be effective in patients with apnea of prematurity, but are often ineffective in older patients. Almitrine can transiently improve ventilatory drive in adults with COPD. However, the administration of almitrine is associated with the development of pulmonary arterial hypertension and peripheral neuropathy; and it does not affect outcome.

Conditions associated with impaired ventilatory drive are common and have a substantial public health impact. For example, large, population-based studies report a prevalence of moderate-severe obstructive sleep apnea of 2-14% of the American population-depending on age and gender—and prevalence may be higher (up to 38% of men) in pulmonary clinic. A significant proportion of patients with OSA have impaired ventilatory drive, particularly those who also have heart failure. There is a large, unmet need for a safe and effective respiratory stimulant in pulmonary and critical care medicine.

Additionally, commonly used narcotic and benzodiazepine medications suppress ventilatory drive. Specifically, they depress the slope of the relationship between $PCO_2$ and minute ventilation. This is a major issue in several important settings. In the operating room and post-anesthesia care setting, patients may have prolonged respiratory depression associated with pain control. This results in prolonged hospitalizations or early, risky discharge and death. In the chronic pain population—in the Veteran's Administration system, for example—death from nocturnal respiratory depression is at epidemic proportions among patients on chronic opiate therapy. Opiate addiction is also at epidemic levels, and hundreds of young people die annually without an effective emergency respiratory stimulant. On the battlefield, medics can have to choose between excruciating pain and risk of death from respiratory depression. In the Intensive Care population, physicians often have to choose between the risk of being on the ventilator for one or more days and the risk of awaking a patient in pain and distress. This is a problem in patients with a baseline blunted $CO_2$ response, such as patients with severe COPD, CF or other obstructive lung disease.

Emergency treatment for narcotic-induced respiratory depression is limited largely to the use of narcotic antagonists, such as naloxone or nalmefene, which are effective at reversing the narcotic induced respiratory depression but also reverse the narcotic mediated pain control, exacerbating the original problem. Further, this treatment is specific to narcotics and is ineffective for benzodiazepine or other sedative or anesthetic induced respiratory depression. A respiratory stimulant that overcomes respiratory depression from any source is needed to address these needs.

SUMMARY

Embodiments described herein relate to compositions and methods of stimulating ventilatory and/or respiratory drive in a subject in need thereof, and particularly relates to the use of a D-cysteine alkyl ester, adducts thereof, and/or pharmaceutically acceptable salt, tautomer, or solvate thereof in compositions and methods of treating breathing diseases and/or disorders associated with impaired ventilator and/or respiratory drive.

In some embodiments, the methods can include stimulating ventilatory and/or respiratory drive in a subject in need thereof by administering to the subject a therapeutically effective amount of a composition that includes a D-cysteine alkyl ester, adduct thereof, and/or pharmaceutically acceptable salt, tautomer, or solvate thereof. The therapeutically effective amount can be an amount effective to stimulate the ventilatory and/or respiratory drive of the subject, including increasing tidal volume, increasing respiratory frequency, increasing minute ventilation, increasing peak inspiratory flow, increasing inspiratory drive, and/or increasing Alveolar-arterial (A-a) gradient.

The composition can be administered to the subject systemically by, for example, topical (e.g., inhalation), enteral (e.g., oral), and/or parenteral (e.g., intravenous injection) administration.

In some embodiments, the D-cysteine alkyl ester can include a compound having the structure of formula:

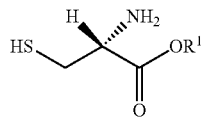

where $R^1$ is a lower alkyl ($C_1$-$C_6$ alkyl); or a pharmaceutically acceptable salt, tautomer, or solvate thereof.

In some embodiments, the D-cysteine alkyl ester can be D-cysteine ethyl ester, an adduct thereof, or a pharmaceutically acceptable salt, tautomer, or solvate thereof.

In other embodiments, the pharmaceutically acceptable salt of a D-cysteine alkyl ester is a hydrochloride salt.

In still other embodiment, the adduct of the D-cysteine alkyl ester can include at least one of an albumin adduct, a glucose adduct, an L-cysteine adduct, an L-glutathione adduct, or an S-nitroso adduct.

In some embodiments, the subject can have or is at increased risk of a breathing disorder, such as respiratory depression, including narcotic, sedative, and/or anesthetic, induced suppression of respiratory drive or ventilatory drive, sleep apnea (central, mixed and obstructive including but not limited to co-existing conditions of heart failure, kidney disease and stroke), sleep-disordered breathing (especially with snoring and arousals), apnea of prematurity, allergies, neurological or neuromuscular diseases (e.g., stroke or amyotrophic lateral sclerosis (ALS)), weakened respiratory muscles, hypoventilation due to stroke, trauma, surgery and/or radiation, obesity-hypoventilation syndrome, primary alveolar hypoventilation syndrome, acquired central hypoventilation syndromes (ACHS), congenital central hypoventilation syndromes (CCHS), chronic bronchitis, Cheyne-Stokes respiration, dyspnea, altitude sickness or acclimatization to high altitude, hypopnea, hypoxia, hypercapnia, cystic fibrosis, chronic obstructive pulmonary disease (COPD), nasal septum deformation, tonsillitis, adenoiditis, and Arnold-Chiari syndrome.

In some embodiments, the composition can be administered to the subject to treat the breathing disorder. For example, the composition can be administered to the subject at an amount effective to prevent the need for mechanical ventilation in subjects with acutely impaired ventilatory and/or respiratory drive because of an acute exacerbation of an underlying lung disease or an acute requirement for narcotic analgesia.

In other embodiments, the subject can have or has an increased risk of respiratory depression that is caused, for example, by an anesthetic, a sleeping aid, a sedative, anxiolytic agent, a hypnotic agent, alcohol, and/or a narcotic. In some embodiments, the narcotic can include an opioid, such as morphine or fentanyl.

In still other embodiments, the composition can be administered to a subject in combination with at least one additional therapeutic agent that changes normal breathing in a subject. The additional agent can be selected from the group consisting of an opioid, doxapram and enantiomers thereof, acetazolamide, almitrine, theophylline, caffeine, methylprogesterone and related compounds, sedatives that decrease arousal threshold in sleep disordered breathing patients, sodium oxybate, benzodiazepine receptor agonists, orexin antagonists, tricyclic antidepressants, serotonergic modulators, adenosine and adenosine receptor and nucleoside transporter modulators, cannabinoids, orexins, melatonin agonists, ampakines, and combinations thereof.

In yet another embodiment, the composition and the agent are separately administered to the subject. In yet another embodiment, the compound and the agent are co-administered to the subject.

In one embodiment, the subject is further administered at least one additional therapeutic agent that changes normal breathing control in the subject. In another embodiment, the additional agent is at least one selected from the group consisting of opioid narcotics, benzodiazepines, sedatives, sleeping aids, hypnotics, propofol, and any combinations thereof.

Still other embodiments relate to a method of preventing or reversing opioid (e.g., fentanyl or morphine) induced respiratory depression in a subject in need thereof. The method includes administering to the subject a therapeutically effective amount of a composition that includes a D-cysteine alkyl ester, adduct thereof, or pharmaceutically acceptable salt, tautomer, or solvate thereof.

In some embodiments, the D-cysteine alkyl ester can include a compound having the structure of formula:

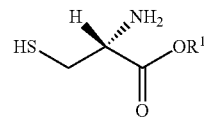

where $R^1$ is a lower alkyl ($C_1$-$C_6$ alkyl); or a pharmaceutically acceptable salt, tautomer, or solvate thereof.

In some embodiments, the D-cysteine alkyl ester can be D-cysteine ethyl ester, an adduct thereof, or a pharmaceutically acceptable salt, tautomer, or solvate thereof.

In other embodiments, the pharmaceutically acceptable salt of a D-cysteine alkyl ester is a hydrochloride salt.

In still other embodiment, the adduct of the D-cysteine alkyl ester can include at least one of an albumin adduct, a glucose adduct, an L-cysteine adduct, an L-glutathione adduct, and an S-nitroso adduct.

In some embodiments, the therapeutically effective amount of the D-cysteine alkyl ester, adduct thereof, or pharmaceutically acceptable salt, tautomer, or solvate thereof is an amount effective to stimulate the ventilatory and/or respiratory drive of the subject, increase tidal volume, increase respiratory frequency, increase minute ventilation, increase peak inspiratory flow, increase inspiratory drive, and/or increase Alveolar-arterial (A-a) gradient.

In other embodiments, the D-cysteine alkyl ester, adduct thereof, or pharmaceutically acceptable salt, tautomer, or solvate thereof is administered to the subject at an amount effective to decrease the deleterious effects of the opioid on breathing, chest-wall rigidity, ventilation-perfusion within the lungs, and arterial blood-gas chemistry without compromising the analgesic effects of the opioid in the subject.

Still other embodiments described herein relate to a composition that includes an opioid capable of inducing respiratory depression in a subject and an amount of a D-cysteine alkyl ester, adduct thereof, or pharmaceutically acceptable salt, tautomer, or solvate thereof effective to prevent the opioid induced respiratory depression when the composition is administered to the subject.

BRIEF DESCRIPTION OF THE DRAWINGS

FIG. 1 illustrates plots and graphs showing that D-CYSee elicits a sustained reversal of morphine-induced respiratory depression without compromising analgesia. D-CYsee reverses the negative effect morphine has on tidal volume. D-CYSee reverses morphine effect on arterial blood gas chemistry including $pO_2$. D-CYSee reverses the negative effect of morphine on gas exchange in the lung. D-CYSee has minimal effects on the analgesic actions of morphine in healthy rats.

FIG. 15 illustrates a graph showing that D-CYSee reverses morphine-induced increases in A-a gradient.

FIG. 18 illustrates plots showing that D-CYSee slightly diminishes 5 mg/kg morphine-induced analgesia.

FIG. 21 illustrates a plot showing that L-Serine ethylester (L-SERee) does not reverse the ventilatory depressant effects of morphine.

FIG. 22 illustrates a plot showing that N-acetyl-L-cysteine methylester (L-NACme) minimally affects the ventilatory effects of morphine.

DETAILED DESCRIPTION

Figure 2:
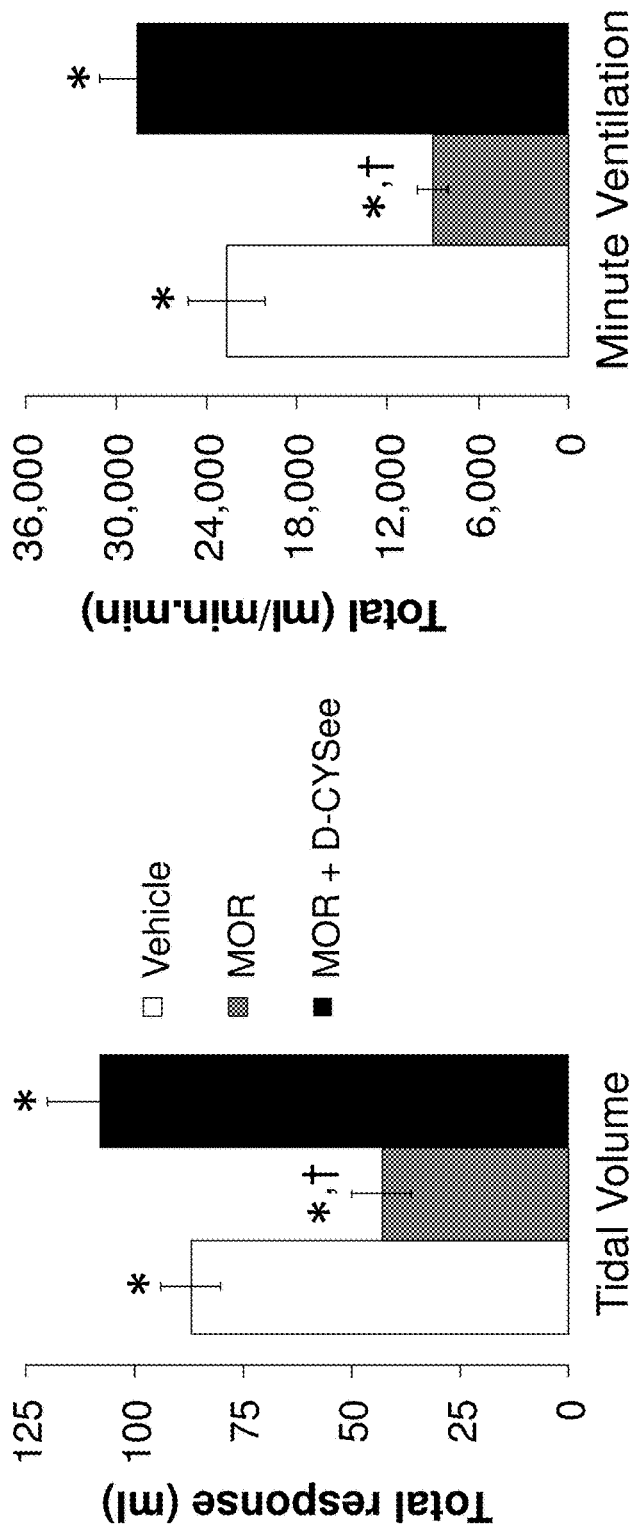
FIG. 2 illustrates graphs showing that the ventilatory responses elicited by a hypoxic-hypercapnic (10% $O_2$, 5% $CO_2$, 85% $N_2$) gas challenge are markedly diminished 2 hours after recovery of baseline ventilator parameters—4 hours post-morphine.

Methods involving conventional molecular biology techniques are described herein. Such techniques are generally known in the art and are described in detail in methodology treatises, such as Current Protocols in Molecular Biology, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the present invention pertains. Commonly understood definitions of molecular biology terms can be found in, for example, Rieger et al., Glossary of Genetics: Classical and Molecular, 5th Edition, Springer-Verlag: New York, 1991, and Lewin, Genes V, Oxford University Press: New York, 1994. The definitions provided herein are to facilitate understanding of certain terms used frequently herein and are not meant to limit the scope of the present invention.

For convenience, certain terms employed in the specification, examples, and appended claims are collected here. Unless defined otherwise, all technical and scientific terms used herein have the same meaning as commonly understood by one of ordinary skill in the art to which this application belongs.

The articles "a" and "an" are used herein to refer to one or to more than one (i.e., to at least one) of the grammatical object of the article. By way of example, "an element" means one element or more than one element.

The terms "comprise," "comprising," "include," "including," "have," and "having" are used in the inclusive, open sense, meaning that additional elements may be included. The terms "such as", "e.g.", as used herein are non-limiting and are for illustrative purposes only. "Including" and "including but not limited to" are used interchangeably.

The term "or" as used herein should be understood to mean "and/or", unless the context clearly indicates otherwise.

The term "about" or "approximately" as used herein refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

It will be noted that the structure of some of the compounds of the application include asymmetric (chiral) carbon or sulfur atoms. It is to be understood accordingly that the isomers arising from such asymmetry are included herein, unless indicated otherwise. Such isomers can be obtained in substantially pure form by classical separation techniques and by stereochemically controlled synthesis. The compounds of this application may exist in stereoisomeric form, therefore can be produced as individual stereoisomers or as mixtures.

The term "isomerism" refers to compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center" whereas a sulfur bound to three or four different substituents, e.g., sulfoxides or sulfinimides, is likewise termed a "chiral center".

The term "chiral isomer" refers to a compound with at least one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has 2n−1 enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Alternatively, when one or more chiral centers are present, a stereoisomer may be characterized as (+) or (−). Absolute configuration refers to the arrangement in space of the substituents attached to the chiral center. The substituents attached to the chiral center under consideration are ranked in accordance with the Sequence Rule of Cahn, Ingold and Prelog. (Cahn et al, Angew. Chem. Inter. Edit. 1966, 5, 385; errata 511; Cahn et al., Angew. Chem. 1966, 78, 413; Cahn and Ingold, J Chem. Soc. 1951 (London), 612; Cahn et al., Experientia 1956, 12, 81; Cahn, J., Chem. Educ. 1964, 41, 116).

The term "geometric isomers" refers to diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules. Further, the structures and other compounds discussed in this application include all atropic isomers thereof.

The term "atropic isomers" refers to a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

The term "apnea" refers to the absence of normal breathing resulting in intermittent stoppages of breathing.

The term "Cheyne-Stokes respiration" refers to a specific pattern of breathing characterized by a crescendo pattern of breathing that results in apneas and/or hypopneas. A hallmark of this condition is that breathing becomes out of phase with blood oxygen levels.

The term "patency" refers to the state or condition of an airway being open or unblocked.

The term "hypopnea" is similar in many respects to apnea; however, breathing does not fully stop but is partially stopped (i.e., less than 100% of normal breathing, but more than 0% of normal breathing). Hypopnea is also referred to herein as "partial apnea" and can be subdivided into obstructive, central or mixed types.

The term "hypoxia" refers to a deficiency in the amount of oxygen, being taken in by an organism, as well as to a deficiency in the amount of oxygen, which is transported to tissues in an organism.

The term "normoxia" refers to a homoeostasis or "normal condition" regarding the amount of oxygen being taken in by an organism, as well as to a homeostasis or "normal condition" with respect to the amount of oxygen which is transported to tissues in an organism.

The phrases "parenteral administration" and "administered parenterally" are art-recognized terms, and include modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrasternal injection and infusion.

The term "treating" is art-recognized and includes inhibiting a disease, disorder or condition in a subject, e.g., impeding its progress; and relieving the disease, disorder or condition, e.g., causing regression of the disease, disorder and/or condition. Treating the disease or condition includes ameliorating at least one symptom of the particular disease or condition, even if the underlying pathophysiology is not affected.

The term "preventing" is art-recognized and includes stopping a disease, disorder or condition from occurring in a subject, which may be predisposed to the disease, disorder and/or condition but has not yet been diagnosed as having it. Preventing a condition related to a disease includes stopping the condition from occurring after the disease has been diagnosed but before the condition has been diagnosed.

The term "pharmaceutical composition" refers to a formulation containing the disclosed compounds in a form suitable for administration to a subject. In some embodiments, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, intranasal, inhalational, and the like. Dosage forms for the topical or transdermal administration of a compound described herein includes powders, sprays, ointments, pastes, creams, lotions, gels, solutions, patches, nebulized compounds, and inhalants. In some embodiments, the compound or active ingredient is mixed under sterile conditions with a pharmaceutically acceptable carrier, and with any preservatives, buffers, or propellants that are required.

The phrase "pharmaceutically acceptable" is art-recognized. In certain embodiments, the term includes compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials, which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compounds of the application are capable of further forming salts. All of these forms are also contemplated herein.

"Pharmaceutically acceptable salt" of a compound means a salt that is pharmaceutically acceptable and that possesses the desired pharmacological activity of the parent compound. For example, the salt can be an acid addition salt. One embodiment of an acid addition salt is a hydrochloride salt. The pharmaceutically acceptable salts can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile being preferred. Lists of salts are found in Remington's Pharmaceutical Sciences, 18th ed. (Mack Publishing Company, 1990).

The compounds described herein can also be prepared as esters, for example pharmaceutically acceptable esters. For example, a carboxylic acid function group in a compound can be converted to its corresponding ester, e.g., a methyl, ethyl, or other ester. Also, an alcohol group in a compound can be converted to its corresponding ester, e.g., an acetate, propionate, or other ester.

The compounds described herein can also be prepared as prodrugs, for example pharmaceutically acceptable prodrugs. The terms "pro-drug" and "prodrug" are used interchangeably herein and refer to any compound, which releases an active parent drug in vivo. Since prodrugs are known to enhance numerous desirable qualities of pharmaceuticals (e.g., solubility, bioavailability, manufacturing, etc.) the compounds can be delivered in prodrug form. Thus, the compounds described herein are intended to cover prodrugs of the presently claimed compounds, methods of delivering the same and compositions containing the same. "Prodrugs" are intended to include any covalently bonded carriers that release an active parent drug in vivo when such prodrug is administered to a subject. Prodrugs are prepared by modifying functional groups present in the compound in such a way that the modifications are cleaved, either in routine manipulation or in vivo, to the parent compound. Prodrugs include compounds wherein a hydroxy, amino, sulfhydryl, carboxy, or carbonyl group is bonded to any group that may be cleaved in vivo to form a free hydroxyl, free amino, free sulfhydryl, free carboxy or free carbonyl group, respectively. Prodrugs can also include a precursor (forerunner) of a compound described herein that undergoes chemical conversion by metabolic processes before becoming an active or more active pharmacological agent or active compound described herein.

Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, ester groups (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds, and the like, as well as sulfides that are oxidized to form sulfoxides or sulfones.

The term "protecting group" refers to a grouping of atoms that when attached to a reactive group in a molecule masks, reduces or prevents that reactivity. Examples of protecting groups can be found in Green and Wuts, Protective Groups in Organic Chemistry, (Wiley, 2.sup.nd ed. 1991); Harrison and Harrison et al., Compendium of Synthetic Organic Methods, Vols. 1-8 (John Wiley and Sons, 1971-1996); and Kocienski, Protecting Groups, (Verlag, $3^{rd}$ ed. 2003).

The term "amine protecting group" is intended to mean a functional group that converts an amine, amide, or other nitrogen-containing moiety into a different chemical group that is substantially inert to the conditions of a particular chemical reaction. Amine protecting groups are preferably removed easily and selectively in good yield under conditions that do not affect other functional groups of the molecule. Examples of amine protecting groups include, but are not limited to, formyl, acetyl, benzyl, t-butyldimethylsilyl, t-butyldiphenylsilyl, t-butyloxycarbonyl (Boc), p-methoxybenzyl, methoxymethyl, tosyl, trifluoroacetyl, trimethylsilyl (TMS), fluorenyl-methyloxycarbonyl, 2-trimethylsilyl-ethyoxycarbonyl, 1-methyl-1-(4-biphenylyl) ethoxycarbonyl, allyloxycarbonyl, benzyloxycarbonyl (CBZ), 2-trimethylsilyl-ethanesulfonyl (SES), trityl and substituted trityl groups, 9-fluorenylmethyloxycarbonyl (FMOC), nitro-veratryloxycarbonyl (NVOC), and the like. Those of skill in the art can identify other suitable amine protecting groups.

Representative hydroxy protecting groups include those where the hydroxy group is either acylated or alkylated such as benzyl, and trityl ethers as well as alkyl ethers, tetrahydropyranyl ethers, trialkylsilyl ethers and allyl ethers.

Additionally, the salts of the compounds described herein, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

The term "solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

The compounds, salts and prodrugs described herein can exist in several tautomeric forms, including the enol and imine form, and the keto and enamine form and geometric isomers and mixtures thereof. Tautomers exist as mixtures of a tautomeric set in solution. In solid form, usually one tautomer predominates. Even though one tautomer may be described, the present application includes all tautomers of the present compounds. A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs.

Tautomerizations can be catalyzed by: Base: 1. deprotonation; 2. formation of a delocalized anion (e.g., an enolate); 3. protonation at a different position of the anion; Acid: 1. protonation; 2. formation of a delocalized cation; 3. deprotonation at a different position adjacent to the cation.

A "patient," "subject," or "host" to be treated by the compounds or methods described herein may mean either a human or non-human animal, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder.

The terms "prophylactic" or "therapeutic" treatment is art-recognized and includes administration to the host of one or more of the subject compounds. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The terms "therapeutic agent", "drug", "medicament", "active ingredient", and "bioactive substance" are art-recognized and include molecules and other agents that are biologically, physiologically, or pharmacologically active substances that act locally or systemically in a patient or subject to treat a disease or condition. The terms include without limitation pharmaceutically acceptable salts thereof and prodrugs. Such agents may be acidic, basic, or salts; they may be neutral molecules, polar molecules, or molecular complexes capable of hydrogen bonding; they may be prodrugs in the form of ethers, esters, amides and the like that are biologically activated when administered into a patient or subject.

The phrase "therapeutically effective amount" or "pharmaceutically effective amount" is an art-recognized term. In certain embodiments, the term refers to an amount of a therapeutic agent that produces some desired effect at a reasonable benefit/risk ratio applicable to any medical treatment. In certain embodiments, the term refers to that amount necessary or sufficient to eliminate, reduce or maintain a target of a particular therapeutic regimen. The effective amount may vary depending on such factors as the disease or condition being treated, the particular targeted constructs being administered, the size of the subject or the severity of the disease or condition. One of ordinary skill in the art may empirically determine the effective amount of a particular compound without necessitating undue experimentation. In certain embodiments, a therapeutically effective amount of a therapeutic agent for in vivo use will likely depend on a number of factors, including: the rate of release of an agent from a polymer matrix, which will depend in part on the chemical and physical characteristics of the polymer; the identity of the agent; the mode and method of administration; and any other materials incorporated in the polymer matrix in addition to the agent.

With respect to any chemical compounds, the present application is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

When an atom or a chemical moiety is followed by a subscripted numeric range (e.g., $C_{1-6}$), it is meant to encompass each number within the range as well as all intermediate ranges. For example, "$C_{1-6}$ alkyl" is meant to include alkyl groups with 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6 carbons.

The term "alkyl" is intended to include both branched (e.g., isopropyl, tert-butyl, isobutyl), straight-chain e.g., methyl, ethyl, propyl, butyl, pentyl, hexyl, heptyl, octyl, nonyl, decyl), and cycloalkyl (e.g., alicyclic) groups (e.g., cyclopropyl, cyclopentyl, cyclohexyl, cycloheptyl, cyclooctyl), alkyl substituted cycloalkyl groups, and cycloalkyl substituted alkyl groups. Such aliphatic hydrocarbon groups have a specified number of carbon atoms. For example, $C_{1-6}$ alkyl is intended to include $C_1$, $C_2$, $C_3$, $C_4$, $C_5$, and $C_6$ alkyl groups. As used herein, "lower alkyl" refers to alkyl groups having from 1 to 6 carbon atoms in the backbone of the carbon chain. "Alkyl" further includes alkyl groups that have oxygen, nitrogen, sulfur or phosphorous atoms replacing one or more hydrocarbon backbone carbon atoms. In certain embodiments, a straight chain or branched chain alkyl has six or fewer carbon atoms in its backbone (e.g., $C_1$-$C_6$ for straight chain, $C_3$-$C_6$ for branched chain), for example four or fewer. Likewise, certain cycloalkyls have from three to eight carbon atoms in their ring structure, such as five or six carbons in the ring structure.

Throughout the description, where compositions are described as having, including, or comprising, specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the compositions and methods described herein remains operable. Moreover, two or more steps or actions can be conducted simultaneously.

All percentages and ratios used herein, unless otherwise indicated, are by weight.

Embodiments described herein relate to compositions and methods of stimulating ventilatory and/or respiratory drive in a subject in need thereof, and particularly relates to the use of a D-cysteine alkyl ester, adducts thereof, and/or pharmaceutically acceptable salts thereof in compositions and methods of treating breathing diseases and/or disorders associated with impaired ventilator and/or respiratory drive.

In some embodiments, the methods can include stimulating ventilatory and/or respiratory drive in a subject in need thereof by administering to the subject a therapeutically effective amount of a composition that includes a D-cysteine alkyl ester, adduct thereof, and/or pharmaceutically acceptable salt, tautomer, or solvate thereof.

It was found that the highly cell permeable alkyl ester forms of D-cysteine (e.g., D-cysteine ethyl ester) and biologically active adducts thereof can elicit a significant reversal of opioid induced respiratory depression. Without being bound by theory, it is believed that the cysteine ethyl ester moiety-sulfur atom is essential for activity against opioid related ventilator depression. It was found that D-cysteine alkyl esters and adducts thereof are potent stimulants of ventilatory and/or respiratory drive that effectively overcome breathing disorders, such as respiratory narcotic-induced respiratory depression and that D-cysteine alkyl esters reverse the deleterious effects of narcotics on ventilation and arterial blood-gas chemistry in a subject in need thereof without impairing, attenuating, and/or adversely affecting narcotic-induced analgesia in the subject.

In addition, it was found that that a D-cysteine alkyl ester does not exhibit the deleterious effects of the corresponding L-isomer, such as increasing upper airway resistance, promoting cystinosis-like effects in animals or having negative cardiovascular effects. Without being bound by theory it is believed that this difference in deleterious effects exhibited by the D and L-isomer is based in part on L-cysteine alkyl esters feeding into metabolic pathways that D-cysteine alkyl esters cannot.

In some embodiments, the D-cysteine alkyl esters, adducts thereof, and pharmaceutically acceptable salts, tautomers, or solvates thereof can be administered to a subject in need thereof at an amount or therapeutically effective amount to stimulate the ventilatory and/or respiratory drive of the subject, including increasing tidal volume, increasing respiratory frequency, increasing minute ventilation, increasing peak inspiratory flow, increasing inspiratory drive, and/or increasing Alveolar-arterial (A-a) gradient.

In some embodiments, the D-cysteine alkyl ester can include a compound having the structure of formula:

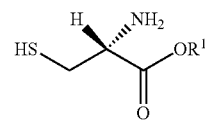

where $R^1$ is a lower alkyl ($C_1$-$C_6$ alkyl); or a pharmaceutically acceptable salt, tautomer, or solvate thereof. In other embodiments, $R^1$ is selected from the group consisting of methyl, ethyl, propyl, and butyl. In certain embodiments, the cysteine alkyl ester can be a D-cysteine ethyl ester, prodrug thereof, or pharmaceutically acceptable salt, tautomer, or solvate thereof. In some embodiments, the pharmaceutical salt of a D-cysteine alkyl ester can include a hydrochloride salt.

In still other embodiment, the adduct of the D-cysteine alkyl ester can be a biologically active adduct and include at least one of an albumin adduct, a glucose adduct, an L-cysteine adduct, an L-glutathione adduct, or an S-nitroso adduct.

Composition comprising a D-cysteine alkyl ester, adduct thereof, and/or pharmaceutically acceptable salt, tautomer, or solvate thereof described herein can be administered to a subject to stimulate ventilatory and/or respiratory drive in a subject in need thereof. In some embodiments, the subject can have or is at increased risk of impaired ventilatory and/or respiratory drive associated with a disorder or breathing disorder, such as respiratory depression, including narcotic, sedative, and/or anesthetic, induced suppression of respiratory drive or ventilatory drive, sleep apnea (central, mixed and obstructive including but not limited to co-existing conditions of heart failure, kidney disease and stroke), sleep-disordered breathing (especially with snoring and arousals), apnea of prematurity, allergies, neurological or neuromuscular diseases (e.g., stroke or amyotrophic lateral sclerosis (ALS)), weakened respiratory muscles, hypoventilation due to stroke, trauma, surgery and/or radiation, obesity-hypoventilation syndrome, primary alveolar hypoventilation syndrome, acquired central hypoventilation syndromes (ACHS), congenital central hypoventilation syndromes (CCHS), chronic bronchitis, Cheyne-Stokes respiration, dyspnea, altitude sickness or acclimatization to high altitude, hypopnea, hypoxia, hypercapnia, cystic fibrosis, chronic obstructive pulmonary disease (COPD), nasal septum deformation, tonsillitis, adenoiditis, and Arnold-Chiari syndrome. The composition can be administered to the subject at an amount effective to treat and/or prevent the breathing disorder or impaired ventilatory and/or respiratory drive associated with the disorder or breathing disorder.

In some embodiments, the composition can be administered to the subject to prevent the need for mechanical ventilation in subjects with acutely impaired ventilatory and/or respiratory drive because of an acute exacerbation of an underlying lung disease or an acute requirement for narcotic analgesia. For example, the subjects can be at-risk subjects with severe, hypercapneic COPD or mixed apnea evident on polysomnography.

In other embodiments, the subject can have or has an increased risk of respiratory depression or suppressed ventilatory drive that is caused, for example, by an anesthetic, a sedative, anxiolytic agent, a hypnotic agent, alcohol, and/or a narcotic. By way of a non-limiting example, narcotic analgesics (e.g., morphine, fentanyl, oxycodone, buprenorphine) are administered to cancer patients to alleviate pain. The dose is often limited by a fear of respiratory depression. In addition, even a partial respiratory depression from these drugs causes hypoxia and a resulting excessive daytime sleepiness that can be debilitating and severely decrease quality of life. General anesthetics can exert a similar depressant effect on respiration and delay a patient's transfer from the operating room to a surgical recovery area. A composition comprising a D-cysteine alkyl ester, adduct thereof, or pharmaceutically acceptable salt, tautomer, or solvate thereof described herein is therefore useful to counteract the lingering effects of the anesthetic, and for restoring adequate respiratory drive to enable the patient to breathe on their own.

In certain embodiments, a therapeutically effective amount of the D-cysteine alkyl ester, adduct thereof, or pharmaceutically acceptable salt, tautomer, or solvate thereof can be administered to a subject in need thereof to prevent or reverse opioid (e.g., fentanyl or morphine) induced respiratory depression in a subject in need thereof. The therapeutically effective amount of the D-cysteine alkyl ester, adduct thereof, or pharmaceutically acceptable salt, tautomer, or solvate thereof is an amount effective to stimulate the ventilatory and/or respiratory drive of the subject, increase tidal volume, increase respiratory frequency, increase minute ventilation, increase peak inspiratory flow, increase inspiratory drive, and/or increase Alveolar-arterial (A-a) gradient.

In other embodiments, the D-cysteine alkyl ester, adduct thereof, or pharmaceutically acceptable salt, tautomer, or solvate thereof is administered to the subject at an amount effective to decreases the deleterious effects of the opioid on breathing, chest-wall rigidity, ventilation-perfusion within the lungs, and arterial blood-gas chemistry without compromising the analgesic effects of the opioid in the subject.

In other embodiments, a composition including the D-cysteine alkyl ester, adduct thereof, or pharmaceutically acceptable salt, tautomer, or solvate thereof can be administered in ambulatory delivery formulations to treat respiratory depression associated with narcotics, analgesics, sedatives, and/or opioids. The subject can be one who is taking and/or over-dosed on the narcotics, analgesics, sedatives, and/or opioids and who is experiencing or at risk of acute respiratory depression. The compositions can be administered to the subject to treat stimulate ventilatory and/or respiratory drive and increase breathing frequency.

In some embodiments, a subject can include a subject with an increased risk of decreased respiratory drive such as a subject with a significant chronic obstructive pulmonary disease or cor pulmonale, and those with a substantially decreased respiratory reserve, hypoxia, hypercapnia, or pre-existing respiratory depression. Elderly, cachectic, or debilitated subjects may have altered pharmacokinetics or altered opioid clearance compared to younger, healthier patients resulting in greater risk for respiratory depression.

In some embodiments, compositions comprising the D-cysteine alkyl ester, adduct thereof, or pharmaceutically acceptable salt, tautomer, or solvate thereof described herein can be administered to the subject in combination with at least one additional compound, agent, and/or therapeutic agent useful for treating the subject or the breathing disorder. These additional compounds, agents, and/or therapeutic agents can include commercially available agents or compounds, known to treat, prevent, or reduce the symptoms of breathing disorders or treat the disorder in the subject.

In some embodiments, the at least one additional therapeutic agent can change normal breathing in a subject. Such additional agents can be selected from the group consisting of an opioid, doxapram and enantiomers thereof, acetazolamide, almitrine, theophylline, caffeine, methylprogesterone and related compounds, sedatives that decrease arousal threshold in sleep disordered breathing patients, sodium oxybate, benzodiazepine receptor agonists, orexin antagonists, tricyclic antidepressants, serotonergic modulators, adenosine and adenosine receptor and nucleoside transporter modulators, cannabinoids, orexins, melatonin agonists, ampakines, and combinations thereof.

In other embodiments, compositions comprising the D-cysteine alkyl ester, adduct thereof, or pharmaceutically acceptable salt, tautomer, or solvate thereof described herein and at least one additional compound has additive, complementary or synergistic effects in the treatment of the breathing disorder or other disorder in the subject. In a non-limiting example, the compositions that include the D-cysteine alkyl ester, adduct thereof, or pharmaceutically acceptable salt, tautomer, or solvate thereof described herein may be used concurrently or in combination with one or more of the following drugs: an opioid (e.g., morphine, oxycodone, fentanyl), doxapram, enantiomers of doxapram, acetazolamide, almitrine, theophylline, caffeine, methylprogesterone and related compounds, sedatives that decrease arousal threshold in sleep disordered breathing patients (e.g., eszopiclone and zolpidem), sodium oxybate, benzodiazepine receptor agonists (e.g., zolpidem, zaleplon, eszopiclone, estazolam, flurazepam, quazepam, temazepam, triazolam), orexin antagonists (e.g., suvorexant), tricyclic antidepressants (e.g., doxepin), serotonergic modulators, adenosine and adenosine receptor and nucleoside transporter modulators, cannabinoids (e.g., but not limited to, dronabinol), orexins, melatonin agonists (e.g., ramelteon) and compounds known as ampakines.

The combination of two or more compounds may refer to a composition wherein the individual compounds are physically mixed or wherein the individual compounds are physically separated. A combination therapy encompasses administering the components separately to produce the desired additive, complementary or synergistic effects.

In one embodiment, the composition comprising the D-cysteine alkyl ester, adduct thereof, or pharmaceutically acceptable salt, tautomer, or solvate thereof described herein and an additional agent are physically mixed in the composition. In another embodiment, the composition comprising the D-cysteine alkyl ester, adduct thereof, or pharmaceutically acceptable salt, tautomer, or solvate thereof described herein and the additional agent are physically separated in the composition.

In one embodiment, compositions comprising the D-cysteine alkyl ester, adduct thereof, or pharmaceutically acceptable salt, tautomer, or solvate thereof described herein is co-administered with a compound that is used to treat another disorder but causes loss of breathing control. In this aspect, compositions comprising the D-cysteine alkyl ester, adduct thereof, or pharmaceutically acceptable salt, tautomer, or solvate thereof described herein block or otherwise reduce depressive effects on normal breathing control caused by the compound with which they are co-administered. An exemplary compound that treats another disorder but depresses breathing control includes but is not limited to anesthetics, sedatives, sleeping aids, anxiolytics, hypnotics, alcohol, and narcotic analgesics. The co-administered compound may be administered individually, or a combined composition as a mixture of solids and/or liquids in a solid, gel or liquid formulation or as a solution, according to methods known to those familiar with the art.

In some embodiments, a composition comprising the D-cysteine alkyl ester, adduct thereof, or pharmaceutically acceptable salt, tautomer, or solvate thereof described herein may be packaged with at least one additional compound useful for treating breathing control disorders. In another embodiment, a composition comprising a D-cysteine alkyl described herein may be packaged with a therapeutic agent known to cause changes in breathing control, such as, but not limited to, anesthetics, sedatives, anxiolytics, hypnotics, alcohol, and narcotic analgesics. A co-package may be based upon, but not limited to, dosage units. For example, a composition can include an opioid capable of inducing respiratory depression in a subject and an amount of a D-cysteine alkyl ester, adduct thereof, or pharmaceutically acceptable salt, tautomer, or solvate thereof effective to prevent the opioid induced respiratory depression when the composition is administered to the subject.

In other embodiment, D-cysteine alkyl ester, adduct thereof, or pharmaceutically acceptable salt, tautomer, or solvate thereof can be administered in combination albumin and/or as an albumin adduct. It was found that D-Cysteine alkyl ester compounds complex with albumin upon administration to a subject and that the complexing albumin can enhance the therapeutic effect of the D-Cysteine alkyl ester in a subject in need thereof. Therefore, in some embodiments, albumin can be administered to the subject in combination with a D-cysteine alkyl ester compound described herein to increase the therapeutic efficacy of the D-cysteine alkyl ester in the subject.

In some embodiments, a subject administered a combination of albumin and a D-Cysteine alkyl ester is a hypoalbuminemic subject. To identify a hypoalbuminemic subject, the subject's serum albumin level can be measured using well known laboratory methods. For example, albumin is generally measured in a subject by a dye-binding technique that utilizes the ability of albumin to form a stable complex with bromocresol green dye (BCG). The serum albumin level can be measured in the plasma, serum, urine or other biological fluid samples obtained from a subject. The normal serum protein level in a human subject is about 6 to about 8 g/dl. In some embodiments, a subject having below 3.5 grams per deciliter of serum albumin is considered to have hypoalmuminemia.

In some embodiments, in addition to a combination of albumin and the D-Cysteine alkyl ester, a subject may be administered one or more agents or medications capable of raising the albumin level in the subject. In alternative embodiments, a subject is administered a combination of one or more agents capable of raising the albumin level in the subject and a D-Cysteine alkyl ester described herein. In certain embodiment, especially where the subject has a kidney condition, an agent capable of raising the albumin level in the subject (e.g., a hypoalbuminemic subject) can include a blood pressure medication employed to prevent a subject from passing albumin out though urine. Exemplary blood pressure medications for use in a method described herein can include but are not limited to captopril and benazepril.

Additional agents capable of raising the albumin level in a subject include immunosuppressive agents to reduce inflammation related albumin loss in the subject. For example, in some embodiments, immunosuppressant agents, such as a corticosteroid, can be administered to a subject in addition to a combination of albumin and the D-Cysteine alkyl ester. Alternatively, an immunosuppressant agent can be administered to a subject in place of albumin in combination with a D-Cysteine alkyl ester.

The D-cysteine alkyl ester, adduct thereof, or pharmaceutically acceptable salt, tautomer, or solvate thereof and/or additional compounds or agents described herein can be provided in a pharmaceutical composition with a pharmaceutically acceptable carrier or excipient. In some embodiment, pharmaceutical compositions that include the D-cysteine alkyl ester, adduct thereof, or pharmaceutically acceptable salt, tautomer, or solvate thereof described herein may be formulated to deliver a dose to the subject of between 1 ng/kg/day and 100 mg/kg/day. In another embodiment, the pharmaceutical compositions may be administered to deliver a dose of D-cysteine alkyl ester, adduct thereof, or pharmaceutically acceptable salt, tautomer, or solvate thereof between 1 ng/kg/day and 500 mg/kg/day.

The relative amounts of the D-cysteine alkyl ester, adduct thereof, or pharmaceutically acceptable salt, tautomer, or solvate thereof, the pharmaceutically acceptable carrier, and any additional ingredients in a pharmaceutical composition can vary, depending upon the identity, size, and condition of the subject treated and further depending upon the route by which the composition is to be administered. By way of example, the composition may comprise between 0.1% and 100% (w/w) active ingredient.

Pharmaceutical compositions that are useful in the methods described herein may be suitably developed for nasal, inhalational, oral, rectal, vaginal, pleural, peritoneal, parenteral, topical, transdermal, pulmonary, intranasal, buccal, ophthalmic, epidural, intrathecal, intravenous or another route of administration. Other contemplated formulations include projected nanoparticles, microspheres, liposomal preparations, coated particles, and polymer conjugates.

In one embodiment, compositions that include the D-cysteine alkyl ester, adduct thereof, or pharmaceutically acceptable salt, tautomer, or solvate thereof described herein are part of a pharmaceutical matrix, which allows for manipulation of insoluble materials and improvement of the bioavailability thereof, development of controlled or sustained release products, and generation of homogeneous compositions. By way of example, a pharmaceutical matrix may be prepared using hot melt extrusion, solid solutions, solid dispersions, size reduction technologies, molecular complexes (e.g., cyclodextrins, and others), microparticulate, and particle and formulation coating processes. Amorphous or crystalline phases may be used in such processes.

The route(s) of administration will be readily apparent to the skilled artisan and will depend upon any number of factors including the type and severity of the disease being treated, the type and age of the veterinary or human patient being treated, and the like.

The formulations of the pharmaceutical compositions described herein may be prepared by any method known or hereafter developed in the art of pharmacology and pharmaceutics. In general, such preparatory methods include the step of bringing the active ingredient into association with a carrier or one or more other accessory ingredients, and then, if necessary or desirable, shaping or packaging the product into a desired single-dose or multi-dose unit.

Although the descriptions of pharmaceutical compositions provided herein are principally directed to pharmaceutical compositions, which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions is contemplated include, but are not limited to, humans and other primates, mammals including commercially relevant mammals such as cattle, pigs, horses, sheep, cats, and dogs.

In one embodiment, the compositions described herein are formulated using one or more pharmaceutically acceptable excipients or carriers Pharmaceutically acceptable carriers, which are useful, include, but are not limited to, glycerol, water, saline, ethanol, recombinant human albumin, solubilized gelatins, and other pharmaceutically acceptable salt solutions, such as phosphates and salts of organic acids. Examples of these and other pharmaceutically acceptable carriers are described in Remington's Pharmaceutical Sciences (1991, Mack Publication Co., New Jersey).

In some embodiments, the carrier may be a solvent or dispersion medium containing, for example, water, ethanol, polyol (for example, glycerol, propylene glycol, and liquid polyethylene glycol, and the like), recombinant human albumin, solubilized gelatins, suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions may be brought about by including in the composition an agent that delays absorption, for example, aluminum monostearate or gelatin.

Formulations of the compositions described herein may be employed in admixtures with conventional excipients, i.e., pharmaceutically acceptable organic or inorganic carrier substances suitable for oral, parenteral, nasal, inhalational, intravenous, subcutaneous, transdermal enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or fragrance-conferring substances and the like. They may also be combined where desired with other active agents, e.g., other analgesic, anxiolytics or hypnotic agents. As used herein, "additional ingredients" include, but are not limited to, one or more ingredients that may be used as a pharmaceutical carrier.

The composition may comprise a preservative from about 0.005% to 2.0% by total weight of the composition. The preservative is used to prevent spoilage in the case of exposure to contaminants in the environment. Examples of preservatives include but are not limited to those selected from the group consisting of benzyl alcohol, sorbic acid, parabens, imidurea and combinations thereof. A particularly preservative is a combination of about 0.5% to 2.0% benzyl alcohol and 0.05% to 0.5% sorbic acid.

The composition can include an antioxidant and a chelating agent which inhibit the degradation of the compound. Examples of antioxidants for some compounds are BHT, BHA, alpha-tocopherol and ascorbic acid in the range of about 0.01% to 0.3% by weight by total weight of the composition. The chelating agent can be present in an amount of from 0.01% to 0.5% by weight by total weight of the composition. Examples of chelating agents include edetate salts (e.g., disodium edetate) and citric acid in the weight range of about 0.01% to 0.20% by weight by total weight of the composition. The chelating agent is useful for chelating metal ions in the composition, which may be detrimental to the shelf life of the formulation.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, acacia, and ionic or non ionic surfactants. Known preservatives include, but are not limited to, methyl, ethyl, or n-propyl para-hydroxybenzoates, ascorbic acid, and sorbic acid. Known sweetening agents include, for example, glycerol, propylene glycol, sorbitol, sucrose, and saccharin.

Liquid solutions of the active ingredient in aqueous or oily solvents may be prepared in substantially the same manner as liquid suspensions, the primary difference being that the active ingredient is dissolved, rather than suspended in the solvent. An "oily" liquid is one which comprises a carbon-containing liquid molecule and which exhibits a less polar character than water. Liquid solutions of the pharmaceutical composition may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, ionic and non-ionic surfactants, and a preservative. Additional excipients, such as fillers and sweetening, flavoring, or coloring agents, may also be included in these formulations.

A pharmaceutical composition may also be prepared, packaged, or sold in the form of oil-in-water emulsion or a water-in-oil emulsion. The oily phase may be a vegetable oil, such as olive or arachis oil, a mineral oil, such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying. Methods for mixing components include physical milling, the use of pellets in solid and suspension formulations and mixing in a transdermal patch, as known to those skilled in the art.

The regimen of administration may affect what constitutes an effective amount. The therapeutic formulations may be administered to the patient either prior to or after the onset of a breathing disorder event or ventilator depressant effects of the opioid. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the D-cysteine alkyl ester, adduct thereof, or pharmaceutically acceptable salt, tautomer, or solvate thereof described herein to a patient, preferably a mammal, more preferably a human, may be carried out using known procedures, at dosages and for periods of time effective to modulate breathing control and/or respiratory and ventilatory drive in the patient. An effective amount of the therapeutic compound sufficient to achieve a therapeutic effect may vary according to factors, such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the patient being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for the D-cysteine alkyl ester, adduct thereof, or pharmaceutically acceptable salt, tautomer, or solvate thereof is from about 0.01 mg/kg to 100 mg/kg of body weight/per day. One of ordinary skill in the art would be able to study the relevant factors and make the determination regarding the effective amount of the therapeutic compound without undue experimentation.

The compositions that include the D-cysteine alkyl ester, adduct thereof, or pharmaceutically acceptable salt, tautomer, or solvate thereof described herein may be administered to an animal, such as a human, as frequently as several times daily, or it may be administered less frequently, such as once a day, once a week, once every two weeks, once a month, or even less frequently, such as once every several months or even once a year or less. It is understood that the amount of composition or D-cysteine alkyl ester, adduct thereof, or pharmaceutically acceptable salt, tautomer, or solvate thereof described herein dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose will be readily apparent to the skilled artisan and will depend upon any number of factors, such as, but not limited to, the type and severity of the disease being treated, the type and age of the animal, etc.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

A medical doctor, e.g., physician or veterinarian, having ordinary skill in the art may readily determine and prescribe the effective amount of the pharmaceutical composition required. For example, the physician or veterinarian could start doses of the compounds employed in the pharmaceutical composition at levels lower than that required in order to achieve the desired therapeutic effect and gradually increase the dosage until the desired effect is achieved.

Other embodiments described herein relate to a method of treating a subject in need thereof, such as a subject without normal ventilation and/or normal breathing control, by administering the compositions comprising the D-cysteine alkyl ester, adduct thereof, or pharmaceutically acceptable salt, tautomer, or solvate thereof described herein, and additionally treating the patient using a device to support breathing. Such devices include, but are not limited to, ventilation devices, CPAP and BiPAP devices.

Mechanical ventilation is a method to mechanically assist or replace spontaneous breathing. Mechanical ventilation is typically used after an invasive intubation, a procedure wherein an endotracheal or tracheostomy tube is inserted into the airway. It is normally used in acute settings, such as in the ICU, for a short period of time during a serious illness. It may also be used at home or in a nursing or rehabilitation institution, if patients have chronic illnesses that require long-term ventilation assistance. The main form of mechanical ventilation is positive pressure ventilation, which works by increasing the pressure in the patient's airway and thus forcing air into the lungs. Less common today are negative pressure ventilators (for example, the "iron lung") that create a negative pressure environment around the patient's chest, thus sucking air into the lungs. Types of mechanical ventilation are: conventional positive pressure ventilation, high frequency ventilation, non-invasive ventilation (non-invasive positive pressure ventilation or NIPPV), proportional assist ventilation (PAV), adaptive servo ventilation (ASV) and neurally adjusted ventilatory assist (NAVA).

Non-invasive ventilation refers to all modalities that assist ventilation without the use of an endotracheal tube. Non-invasive ventilation is primarily aimed at minimizing patient discomfort and the complications associated with invasive ventilation, and is often used in cardiac disease, exacerbations of chronic pulmonary disease, sleep apnea, and neuromuscular diseases. Non-invasive ventilation refers only to the patient interface and not the mode of ventilation used; modes may include spontaneous or control modes and may be either pressure or volume cycled modes.

Some commonly used modes of NIPPV include continuous positive airway pressure (CPAP). This kind of machine has been used mainly by patients for the treatment of sleep apnea at home, but now is in widespread use across intensive care units as a form of ventilatory support. The CPAP machine stops upper airway obstruction by delivering a stream of compressed air via a hose to a nasal pillow, nose mask or full-face mask, splinting the airway open (keeping it open under air pressure) so that unobstructed breathing becomes possible, reducing and/or preventing apneas and hypopneas. When the machine is turned on, but prior to the mask being placed on the head, a flow of air comes through the mask. After the mask is placed on the head, it is sealed to the face and the air stops flowing. At this point, it is only the air pressure that accomplishes the desired result. This has the additional benefit of reducing or eliminating the extremely loud snoring that sometimes accompanies sleep apnea.

Bi-level positive airway pressure (BIPAP) alternate between inspiratory positive airway pressure (IPAP) and a lower expiratory positive airway pressure (EPAP), triggered by patient effort. On many such devices, backup rates may be set, which deliver IPAP pressures even if patients fail to initiate a breath.

The invention is further illustrated by the following example, which is not intended to limit the scope of the claims.

EXAMPLE

A novel class of thiol-based L-cysteine and D-cysteine respiratory stimulants was evaluated. It was found that erythrocytic hemoglobin transports not only $CO_2$ and $O_2$, but also thiol-bound nitric oxide (NO), and that erythrocytic thiol-bound NO content decays logarithmically as a function of changes in oxyhemoglobin saturation. Thiol-containing compounds, such as glutathione or N-acetylcysteine (NAC) accelerate loss of NO from deoxyhemoglobin and can serve as potent respiratory stimulants, increasing minute ventilation in humans and animals. N-acetylcysteine signals erythrocytic hemoglobin desaturation and augments hypoxia-induced increases minute ventilation. Relative to placebo, humans receiving oral NAC three times daily had a three-fold greater increase in minute ventilation (24±4% versus 8±3%) when exposed acutely to isocapnic hypoxia. However, high NAC doses were required. The details of this pathway were worked out in both rat and transgenic mouse models.

To target this pathway, thiol-containing L-cysteine ethyl ester and D-cysteine ethyl ester compounds were screened as respiratory stimulants. Screenings show that D-cysteine ethyl ester compounds can be used as a novel treatment option for COPD and other pulmonary patients with acute respiratory depression. The principal target population can include patients with impaired ventilatory and/or respiratory drive who are at risk for requiring mechanical ventilation because of either an acute exacerbation of underlying lung disease or an acute requirement for narcotic analgesia and/or patients experiencing ventilator depressant related to opioid use.

FIG. 1 illustrates that D-CYSee elicits a sustained reversal of morphine-induced respiratory depression without compromising analgesia. (A) D-CYsee reverses the negative effect morphine has on tidal volume. (B) D-CYSee reverses morphine effect on arterial blood gas chemistry including $pO_2$ (C) D-CYSee reverses the negative effect of morphine on gas exchange in the lung. (D) D-CYSee has minimal effects on the analgesic actions of morphine in healthy rats.

FIG. 2 illustrates that the ventilatory responses elicited by a hypoxic-hypercapnic (10% $O_2$, 5% $CO_2$, 85% $N_2$) gas challenge are markedly diminished 2 hours after recovery of baseline ventilator parameters—4 hours post-morphine. Injection of D-CYS33 (20 umol/kg, IV) given 15 min after the injection of morphine prevents the delayed reduction in the hypoxic-hypercapnic responses.

Figure 3:
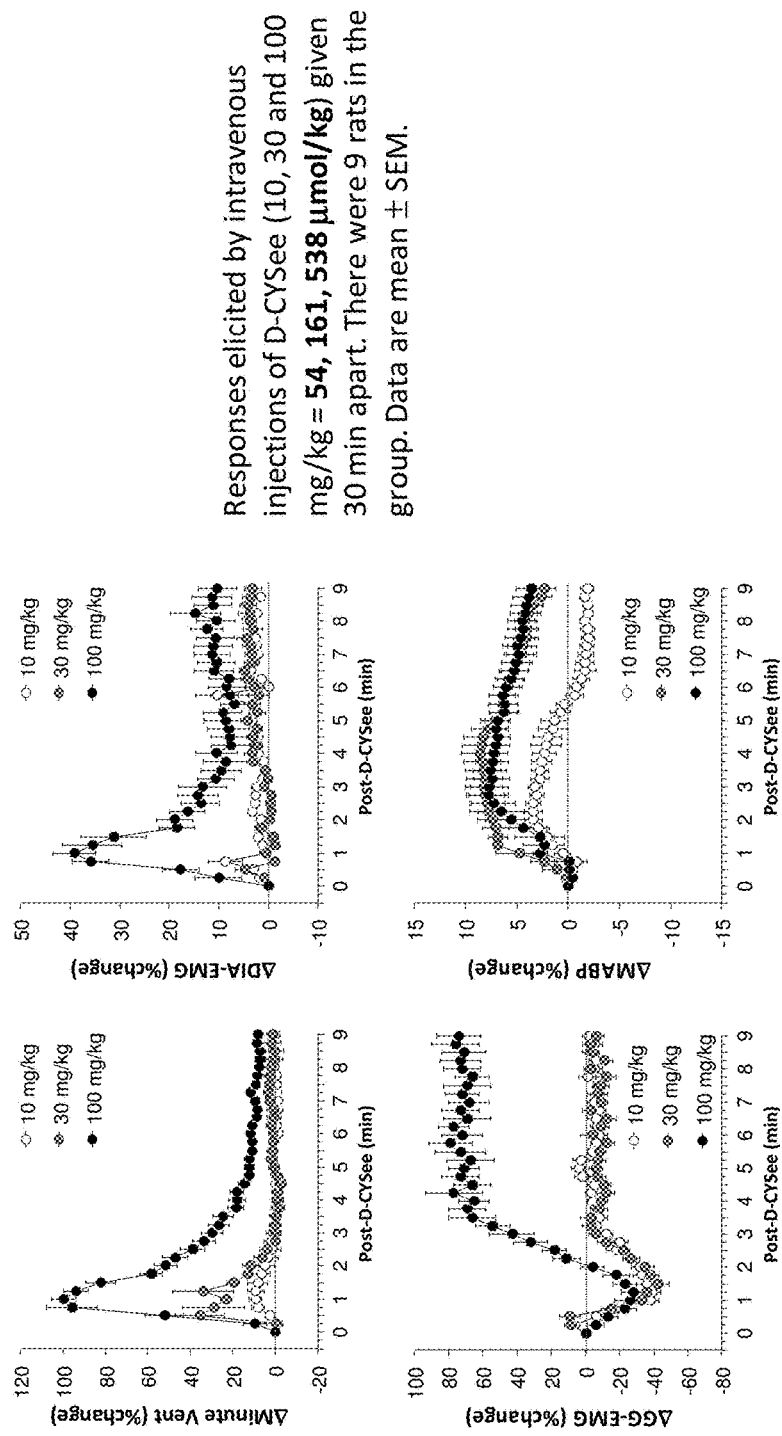
FIG. 3 illustrates plots showing that D-CYSee elicits substantial increases in minute ventilation, diaphragmatic EMG (DIA-EMG), genioglossus-EMG (GG-EMG) with minor changes in mean arterial blood pressure (MABP) in isoflurane-anesthetized naïve rats.

FIG. 3 illustrates that D-CYSee elicits substantial increases in minute ventilation, diaphragmatic EMG (DIA-EMG), genioglossus-EMG (GG-EMG) with minor changes in mean arterial blood pressure (MABP) in isoflurane-anesthetized naïve rats. Beneficial effects of D-CYSee involve an increased force of breathing and increased GG-EMG which would promote forward movement of the tongue and opening of the airway. Responses elicited by intravenous injections of D-CYSee (10, 30 and 100 mg/kg=54, 161, 538 mol/kg) given 30 min apart. There were 9 rats in the group. Data mean±SEM.

Figure 4:
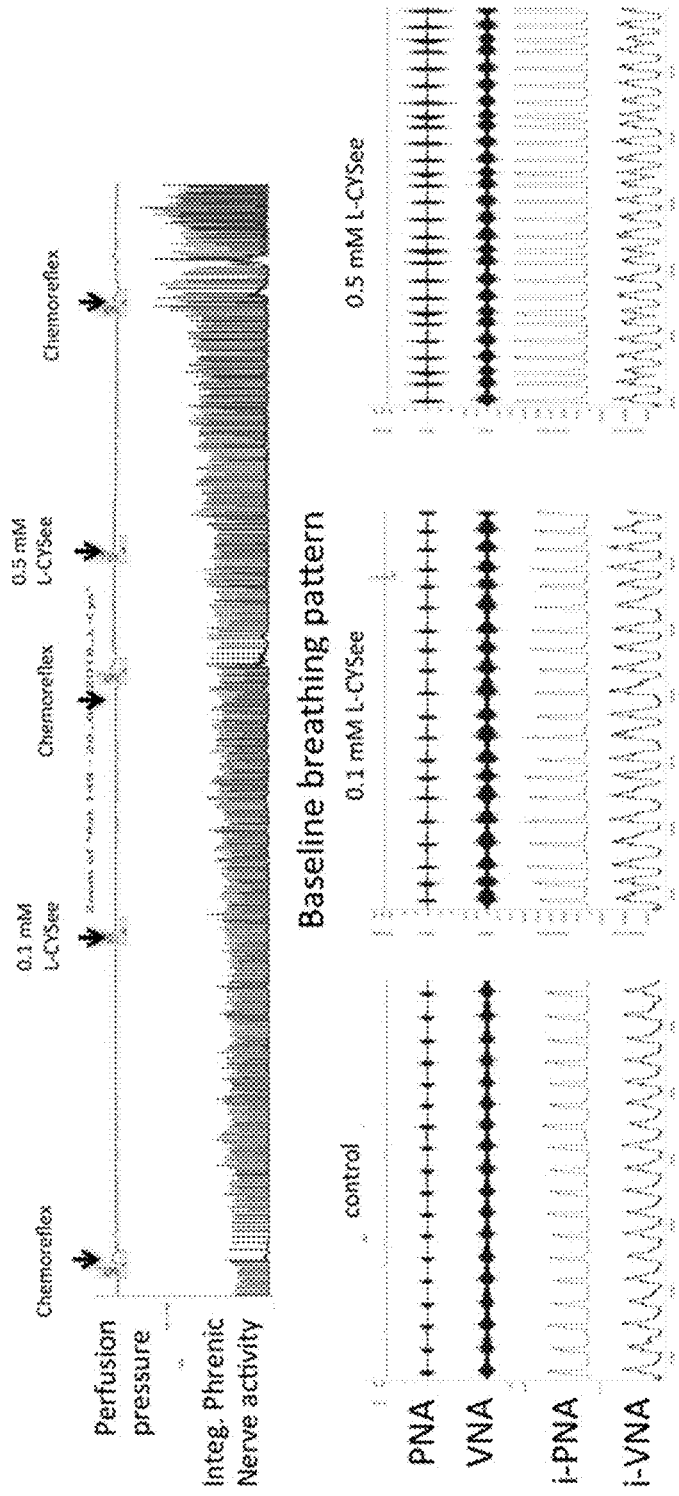
FIG. 4 illustrates plots showing that L-CYSee markedly increases the amplitude of phrenic nerve discharge in the in situ rat brainstem preparation and a direct increase in the force of breathing.

FIG. 4 illustrates that L-CYSee markedly increases the amplitude of phrenic nerve discharge in the in situ rat brainstem preparation and a direct increase in the force of breathing.

Figure 5:
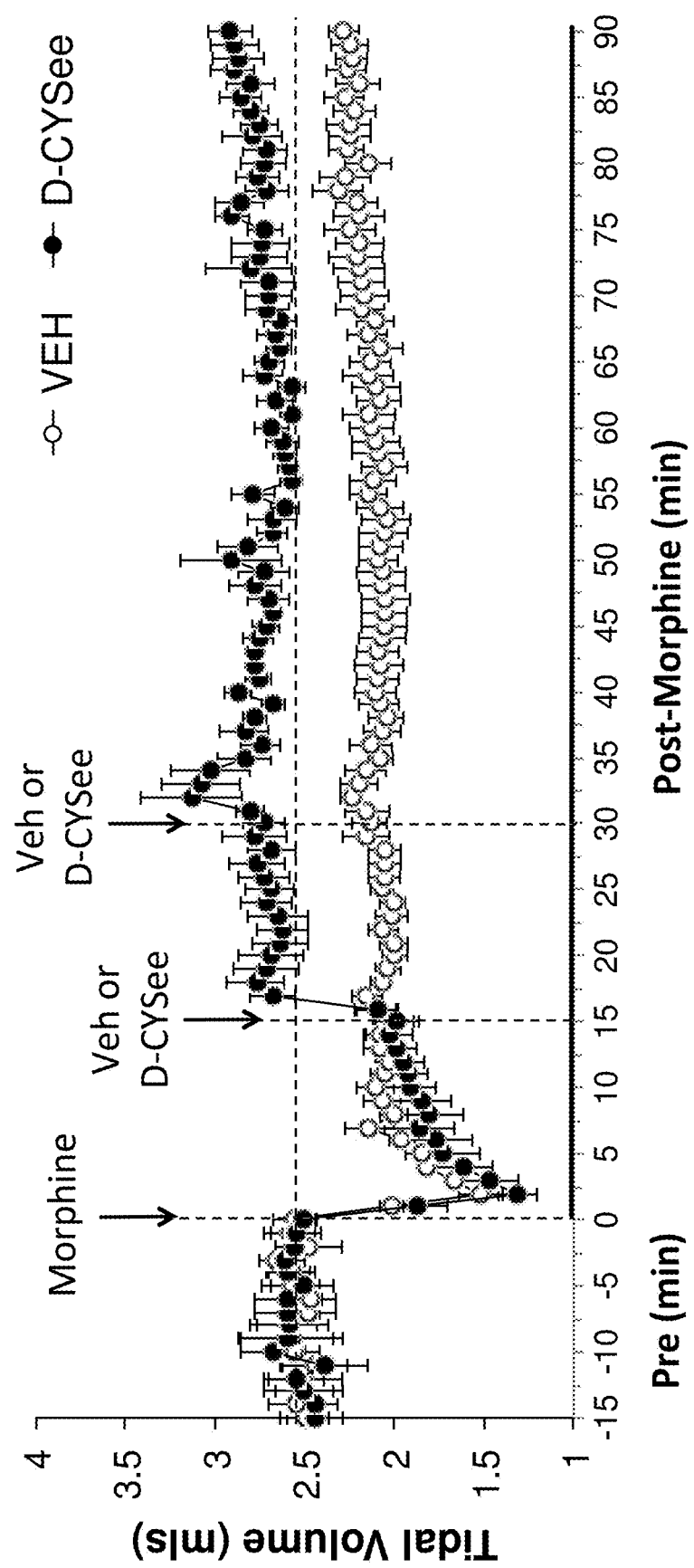
FIG. 5 illustrates a plot showing that D-CYSee elicits a sustained reversal of morphine-induced decrease in Tidal Volume.

FIG. 5 illustrates that D-CYSee elicits a sustained reversal of morphine-induced decrease in Tidal Volume. Changes in tidal volume elicited by bolus injections of vehicle (VEH) or D-CYSee (2×500 mol/kg, iv) in rats which had received a bolus dose of morphine (10 mg/kg, iv). There were 9 rats in each group. Data are presented as mean±SEM.

Figure 6:
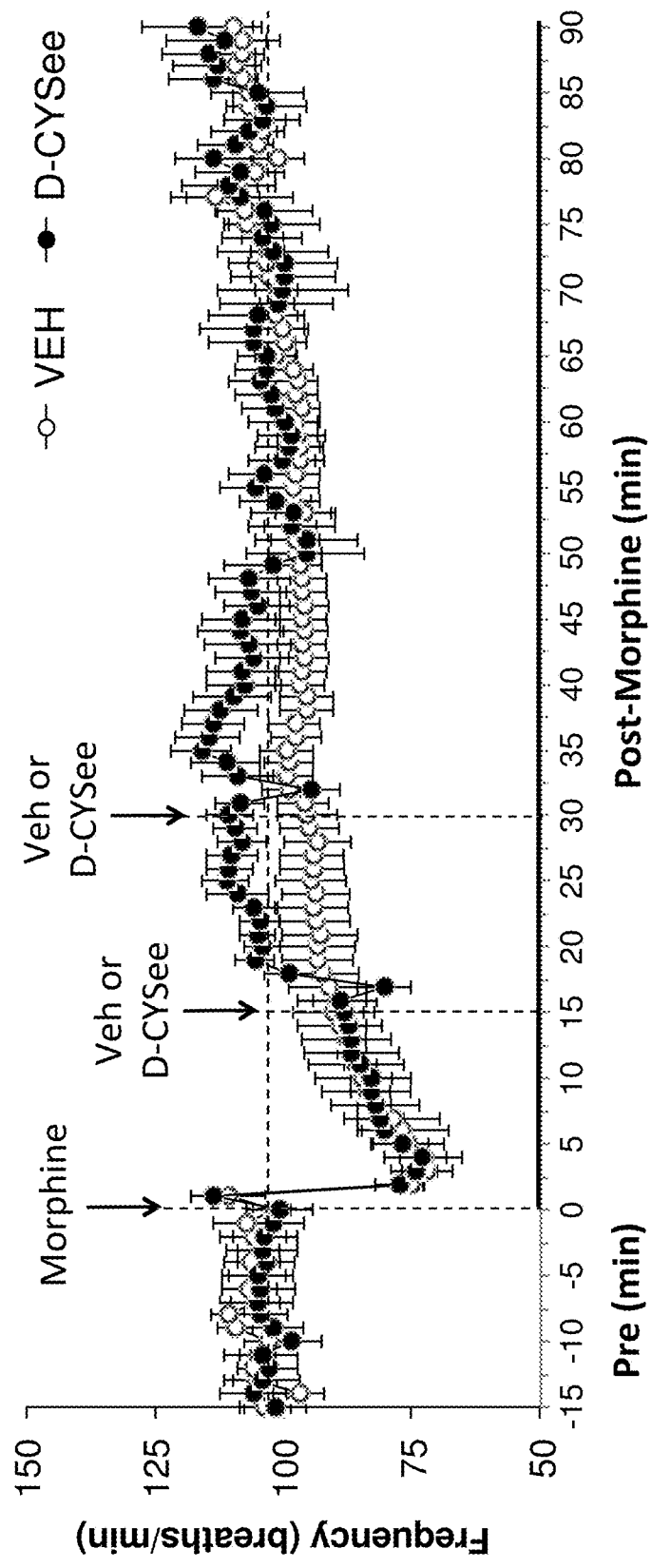
FIG. 6 illustrates a plot showing that morphine-induced suppression of frequency of breathing are not sustained—D-CYSee elicits slight positive effects.

FIG. 6 illustrates that morphine-induced suppression of frequency of breathing are not sustained—D-CYSee elicits slight positive effects. Changes in frequency of breathing elicited by bolus injections of vehicle (VEH) or D-CYSee (2×500 mol/kg, iv) in rats which had received a bolus dose of morphine (10 mg/kg, iv). There were 9 rats in each group. Data are presented as mean±SEM.

Figure 7:
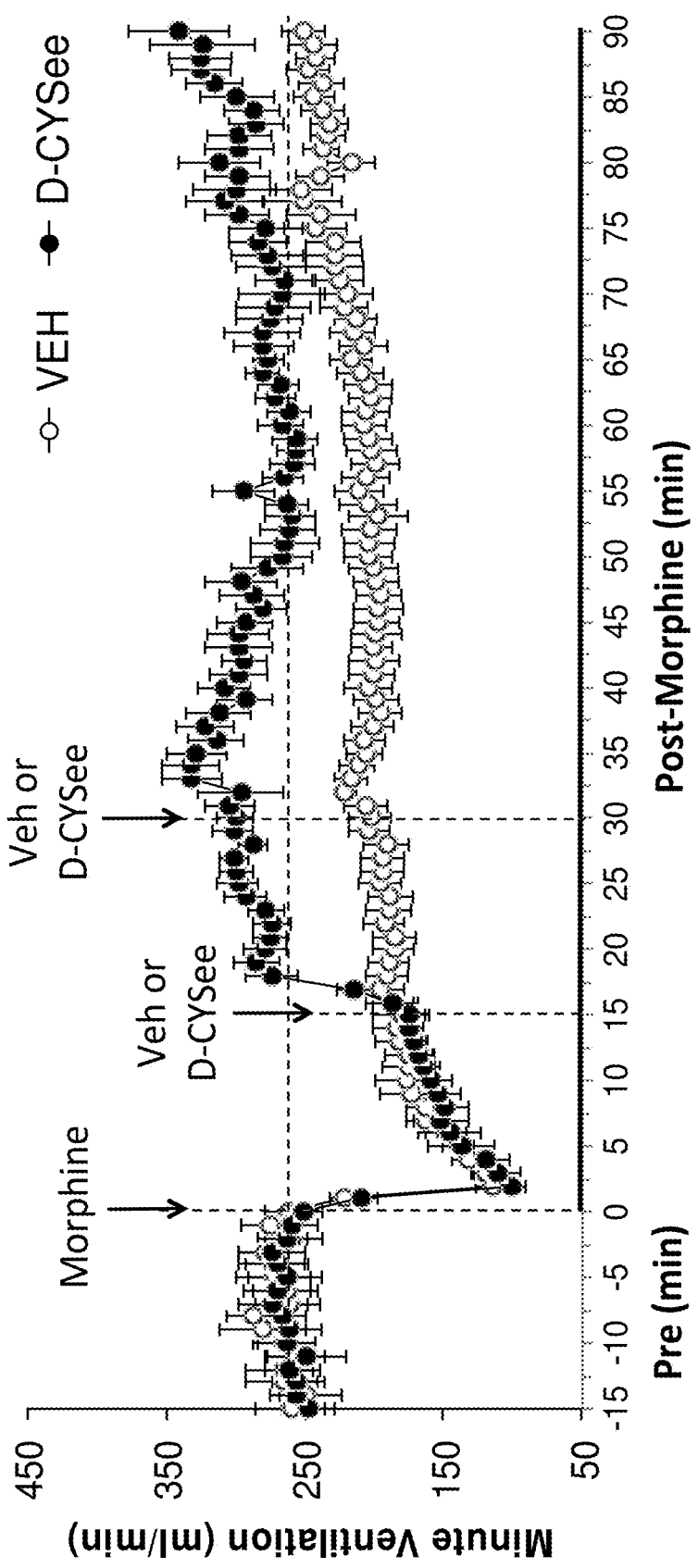
FIG. 7 illustrates a plot showing that D-CYSee elicits a sustained reversal of morphine-induced decrease in Minute Ventilation.

FIG. 7 illustrates that D-CYSee elicits a sustained reversal of morphine-induced decrease in Minute Ventilation. Changes in minute ventilation elicited by bolus injections of vehicle (VEH) or D-CYSee (2×500 mol/kg, iv) in rats which had received a bolus dose of morphine (10 mg/kg, iv). There were 9 rats in each group. Data are presented as mean±SEM.

Figure 8:
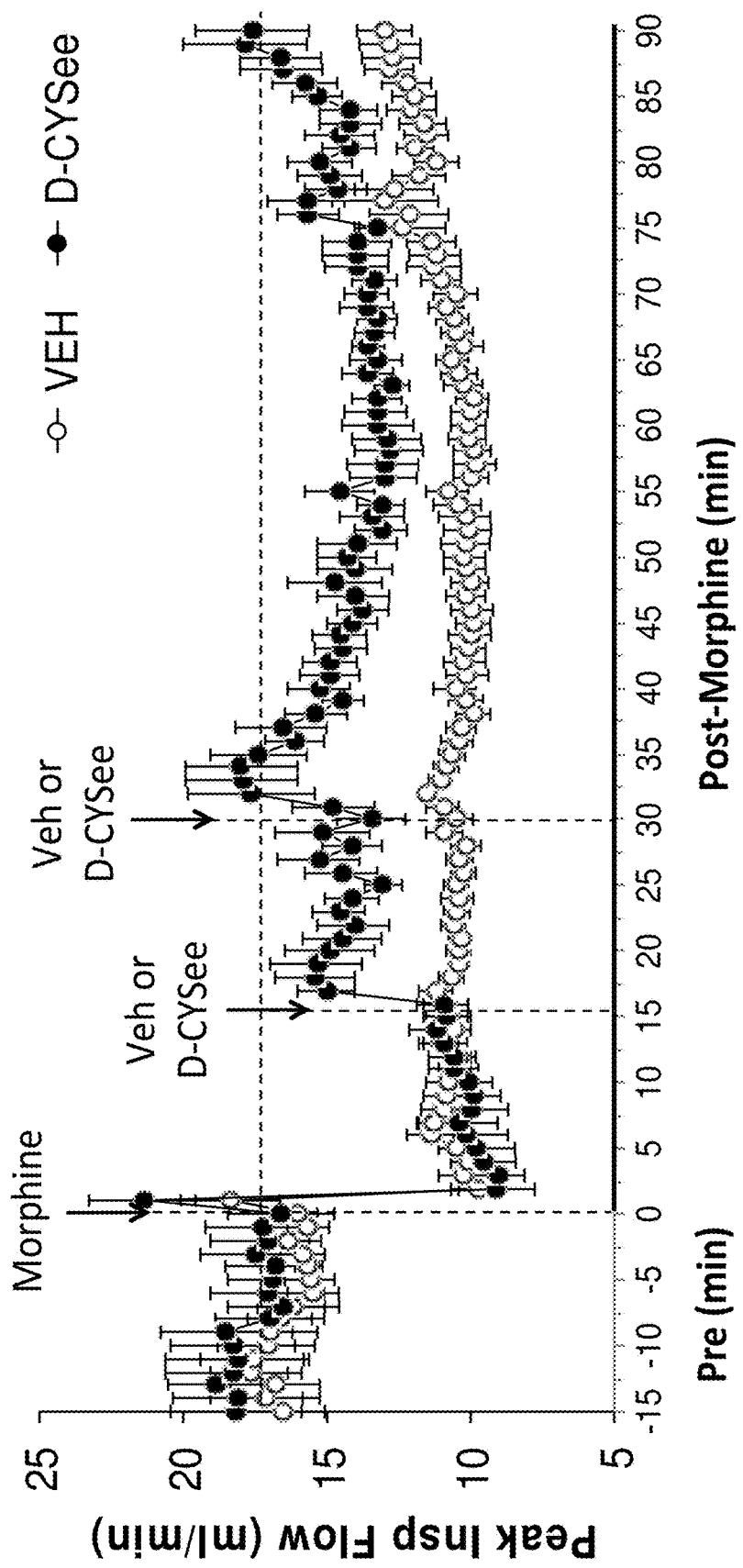
FIG. 8 illustrates a plot showing that D-CYSee elicits a sustained reversal of morphine-induced decrease in Peak Inspiratory Flow.

FIG. 8 illustrates that D-CYSee elicits a sustained reversal of morphine-induced decrease in Peak Inspiratory Flow. Changes in peak inspiratory flow (PIF) elicited by bolus injections of vehicle (VEH) or D-CYSee (2×500 mol/kg, iv) in rats which had received a bolus dose of morphine (10 mg/kg, iv). There were 9 rats in each group. Data are presented as mean±SEM.

Figure 9:
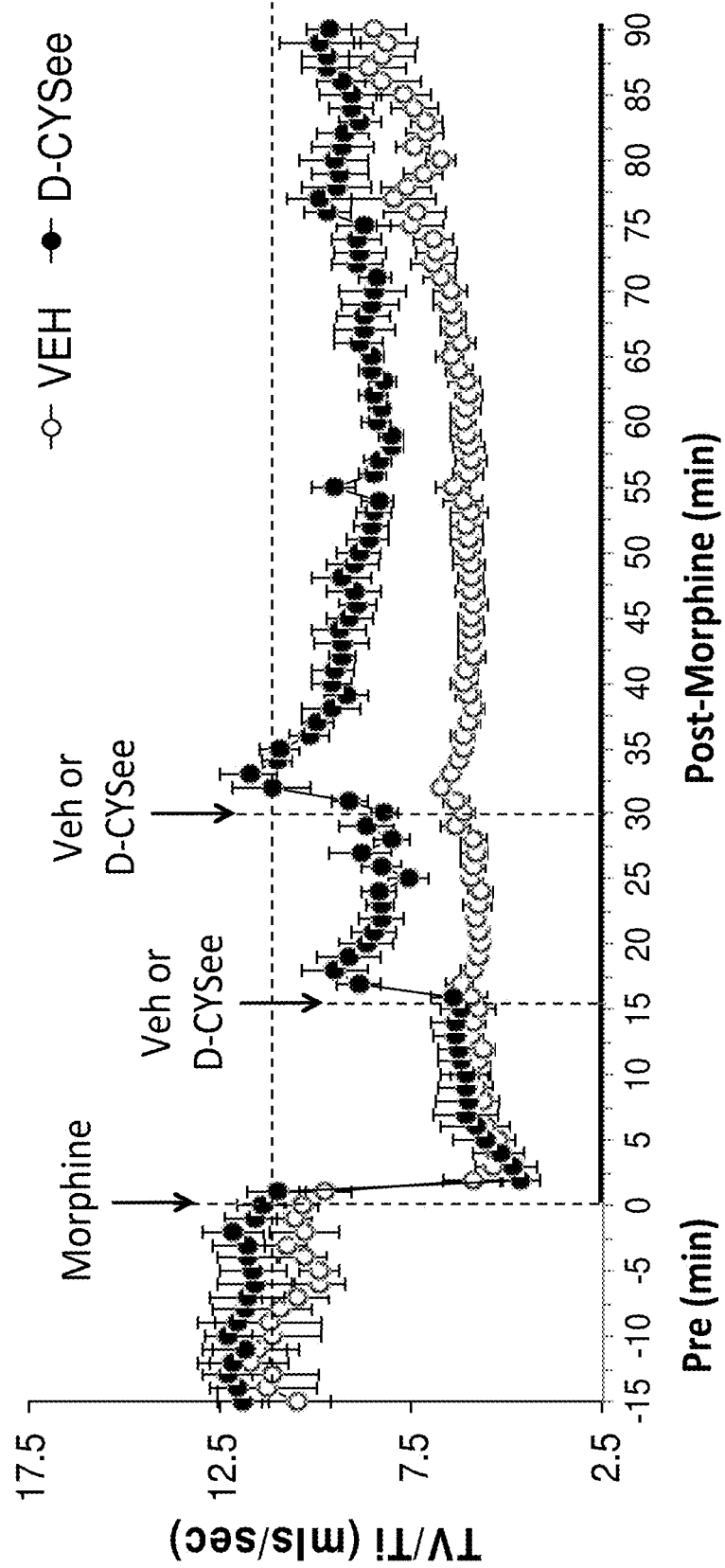
FIG. 9 illustrates a plot showing that D-CYSee elicits a sustained reversal of morphine-induced decrease in Inspiratory Drive.

FIG. 9 illustrates that D-CYSee elicits a sustained reversal of morphine-induced decrease in Inspiratory Drive. Changes in inspiratory drive (TV/Ti) elicited by bolus injections of vehicle (VEH) or D-CYSee (2×500 mol/kg, iv) in rats which had received a bolus dose of morphine (10 mg/kg, iv). There were 9 rats in each group. Data are presented as mean±SEM. TV, Tidal volume. Ti, Inspiratory duration.

Figure 10:
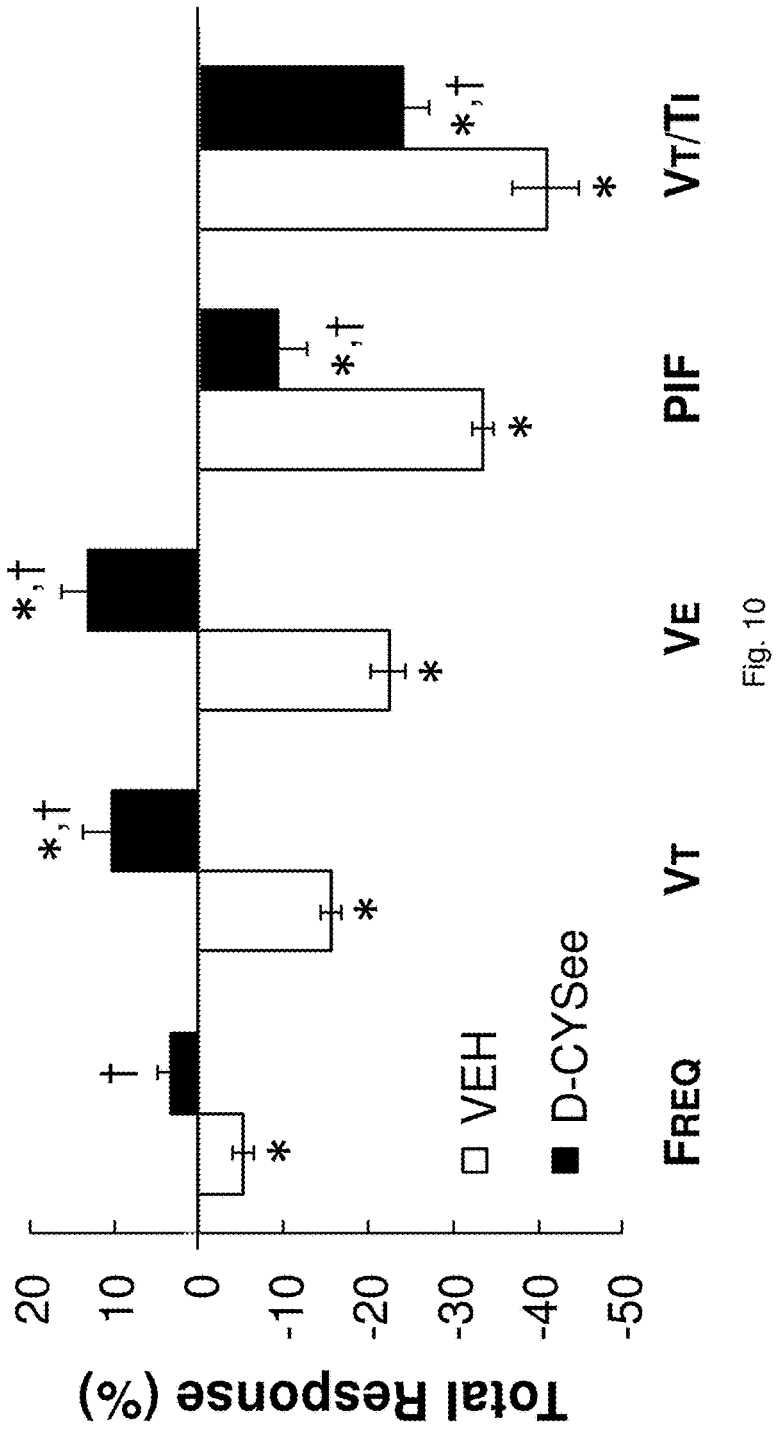
FIG. 10 illustrates a graph showing that D-CYSee reverses the total (area under the curve) ventilatory-depressant effects of morphine.

FIG. 10 illustrates D-CYSee reverses the total (area under the curve) ventilatory-depressant effects of morphine. Ventilatory responses elicited by vehicle (saline) or D-CYSee (2×500 mol/kg, iv) in rats which had received a bolus dose of morphine (10 mg/kg, iv). There were 9 rats in each group. Data are presented as mean±SEM. *$P<0.05$, difference from pre. †$P<0.05$, D-Cysteine ethylester (D-CYSee) versus vehicle.

Figure 11:
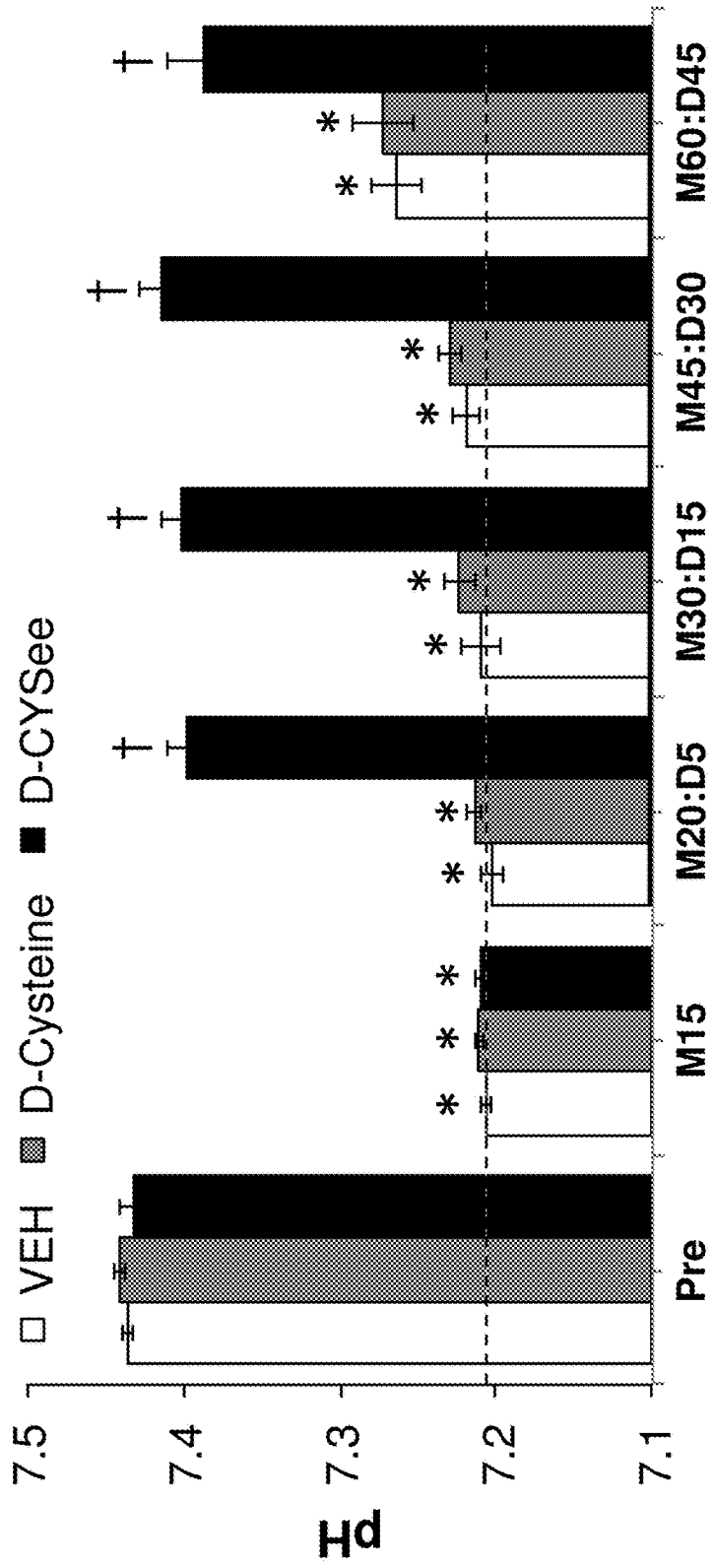
FIG. 11 illustrates a graph showing that D-CYSee reverses morphine-induced decreases in blood pH.

FIG. 11 illustrates that D-CYSee reverses morphine-induced decreases in blood pH. Values were recorded 15, 20, 30, 45 and 60 minutes after injection of morphine. D-CYSee was given immediately after drawing blood at the 15 min (M15) post-morphine time-point. The first blood sample for analysis of the effects of D-cysteine or D-CYSee was taken 20 min after morphine administration and 5 minutes after test drug injection (M20:D5). Effects of D-Cystein (500 mol/kg, iv) or D-CYSee (500 mol/kg, iv) on arterial blood pH in rats which had received morphine (10 mg/kg, iv). Data are presented as mean±SEM (n=9 rats per group). *$P<0.05$, difference from pre. †$P<0.05$, D-Cysteine ethylester (D-CYSee) versus vehicle.

Figure 12:
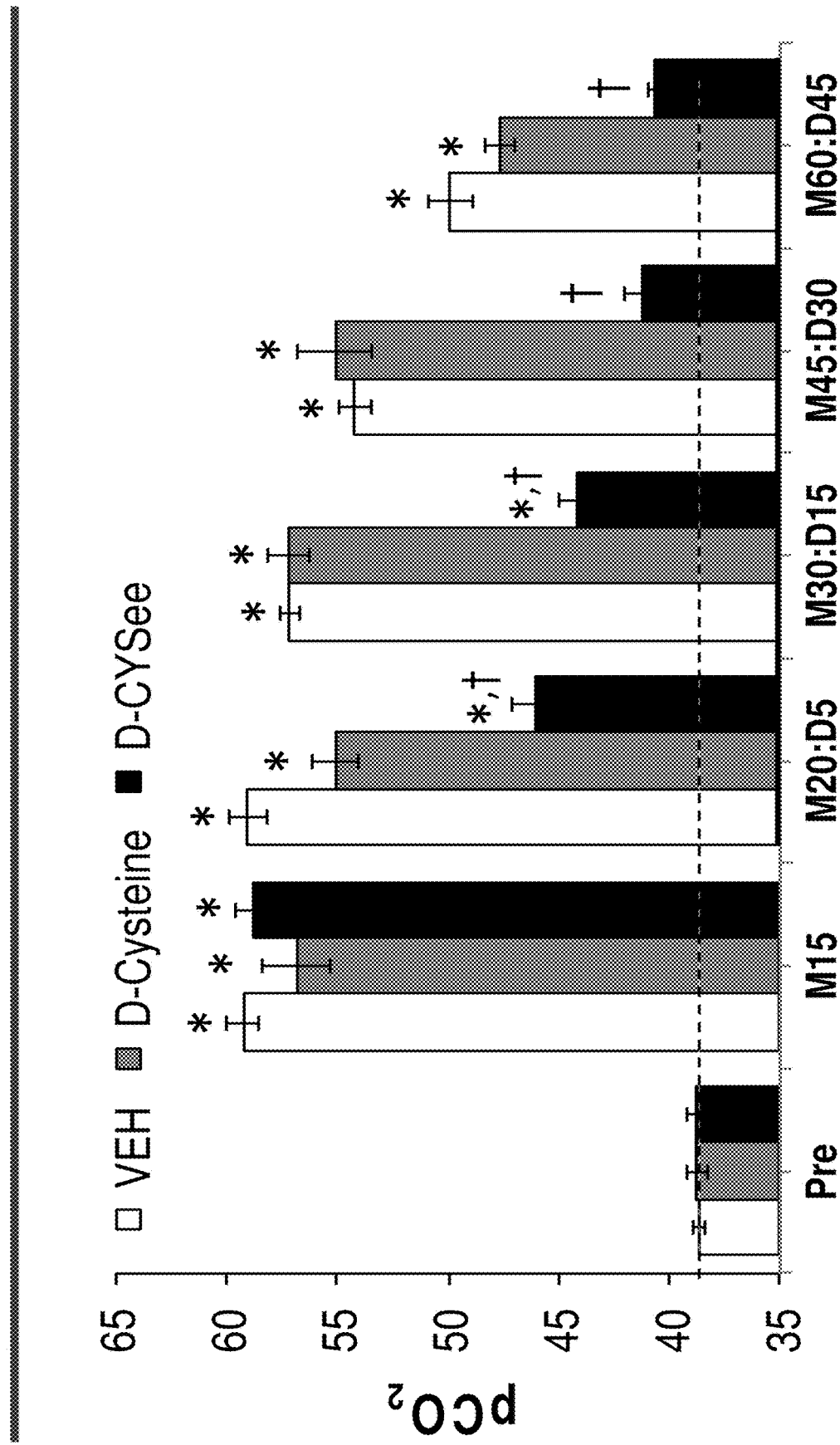
FIG. 12 illustrates a graph showing D-CYSee reverses morphine-induced increases in $pCO_2$.

FIG. 12 illustrates D-CYSee reverses morphine-induced increases in $pCO_2$. Effects of D-Cysteine (500 μmol/kg, iv) or D-CYSee (500 mol/kg, iv) on arterial blood $pCO_2$ in rats which had received morphine (10 mg/kg, iv). Data are presented as mean±SEM (n=9 rats per group). *$P<0.05$, difference from pre. †$P<0.05$, D-Cysteine ethylester (D-CYSee) versus vehicle.

Figure 13:
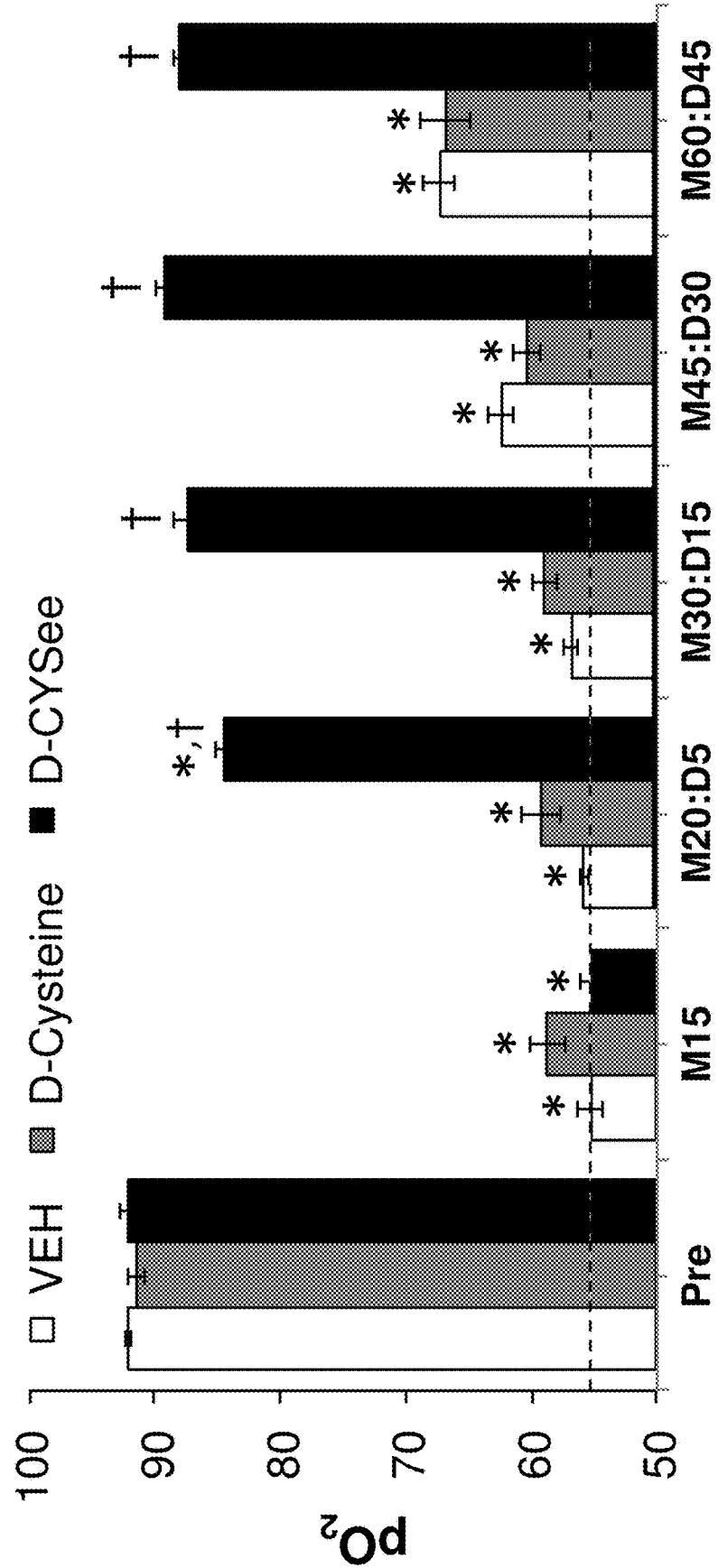
FIG. 13 illustrates a graph showing that D-CYSee reverses morphine-induced decreases in $pO_2$.

FIG. 13 illustrates D-CYSee reverses morphine-induced decreases in $pO_2$. Effects of D-Cysteine (500 mol/kg, iv) or D-CYSee (500 mol/kg, iv) on arterial blood $pO_2$ in rats which had received morphine (10 mg/kg, iv). Data are presented as mean±SEM (n=9 rats per group). *$P<0.05$, difference from pre. †$P<0.05$, D-Cysteine ethylester (D-CYSee) versus vehicle.

Figure 14:
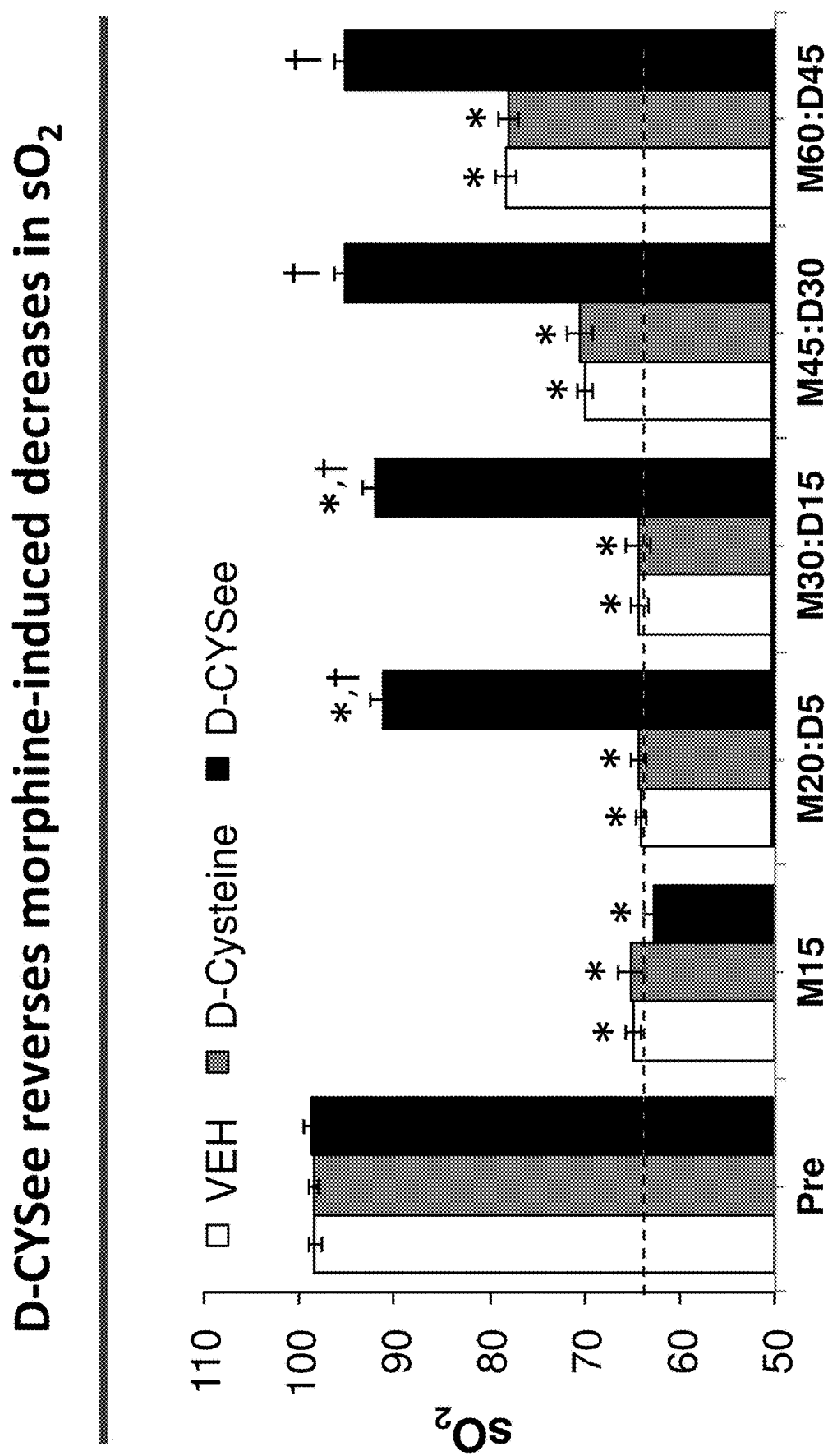
FIG. 14 illustrates a graph showing that D-CYSee reverses morphine-induced decreases in $sO_2$.

FIG. 14 illustrates D-CYSee reverses morphine-induced decreases in 502. Effects of D-Cysteine (500 mol/kg, iv) or D-CYSee (500 mol/kg, iv) on arterial blood $sO_2$ in rats which had received morphine (10 mg/kg, iv). Data are presented as mean±SEM (n=9 rats per group). *$P<0.05$, difference from pre. †$P<0.05$, D-Cysteine ethylester (D-CYSee) versus vehicle.

FIG. 15 illustrates D-CYSee reverses morphine-induced increases in A-a gradient. The Alveolar-arterial (A-a) gradient is a measure of the difference between alveolar (A) and the arterial (a) concentrations of oxygen. It is used to diagnose the source of hypoxemia and helps to assess the integrity of alveolar capillary unit. In conditions of ventilation perfusion mismatch, oxygen is not effectively transferred from the alveoli to the blood, which results in elevated A-a gradient. An elevated A-a gradient reflects increased ventilation-perfusion mismatch. Effects of D-Cysteine (500 mol/kg, iv) or D-CYSee (500 mol/kg, iv) on A-a gradient in rats which had received morphine (10 mg/kg, iv). Data are presented as mean±SEM (n=9 rats per group). *$P<0.05$, difference from pre. †$P<0.05$, D-Cysteine ethylester (D-CYSee) versus vehicle.

Figure 16:
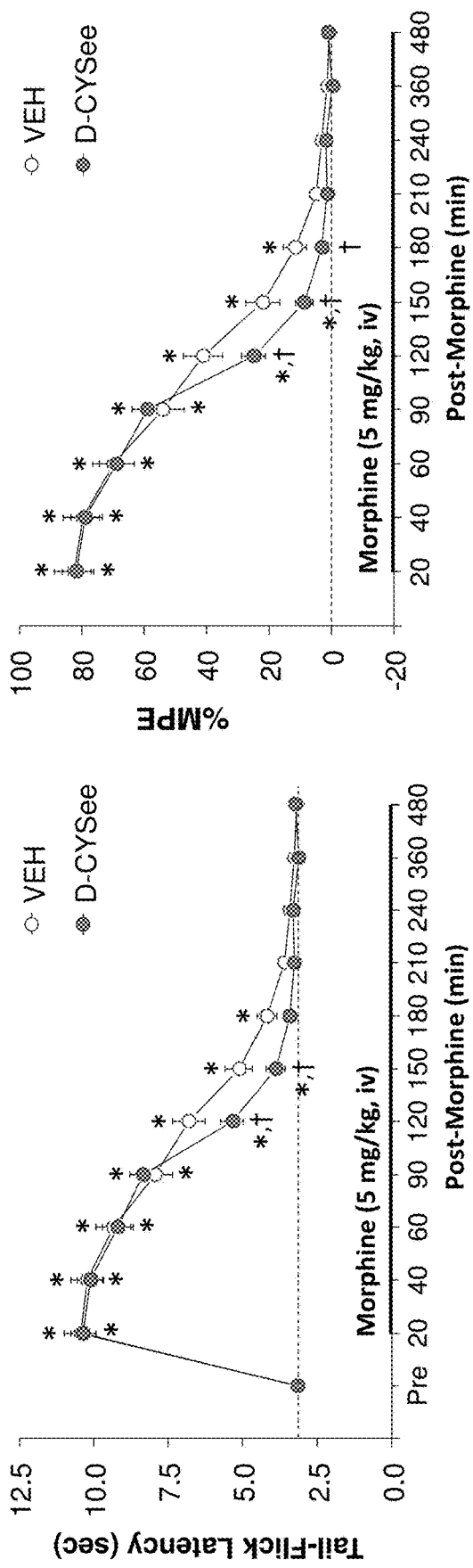
FIG. 16 illustrates plots showing that D-CYSee slightly diminishes 5 mg/kg morphine-induced analgesia.

FIG. 16 illustrates that D-CYSee slightly diminishes 5 mg/kg morphine-induced analgesia. Tail-Flick Latency (TFL)-time at which the rat will flick the tail upon exposure to a beam of radiant heat. D-CYSee (500 umol/kg, iv) or vehicle (saline, iv) were injected to Sprague-Dawley rats and after 15 min, TFL was determined (Pre value). Immediately afterwards, all rats received a bolus injection of morphine (5 mg/kg, iv) and TFL monitored at regular times thereafter. A cut-off latency of 12 sec was chosen to limit heat injury. Data are expressed as TFL (sec) and % MPE [% Maximum Possible Effect=((Morphine-induced TFL-pre-morphine TFL)/(Cut-off Latency-pre-drug latency))*100. Effects of D-CYSee (500 mol/kg, iv) on Tail-Flick latency in rats which had either received saline or morphine (5 mg/kg, iv). Data are presented as mean±SEM (n=9 rats per group). *$P<0.05$, difference from pre. †$P<0.05$, D-Cysteine ethylester (D-CYSee) versus vehicle.

Figure 17:
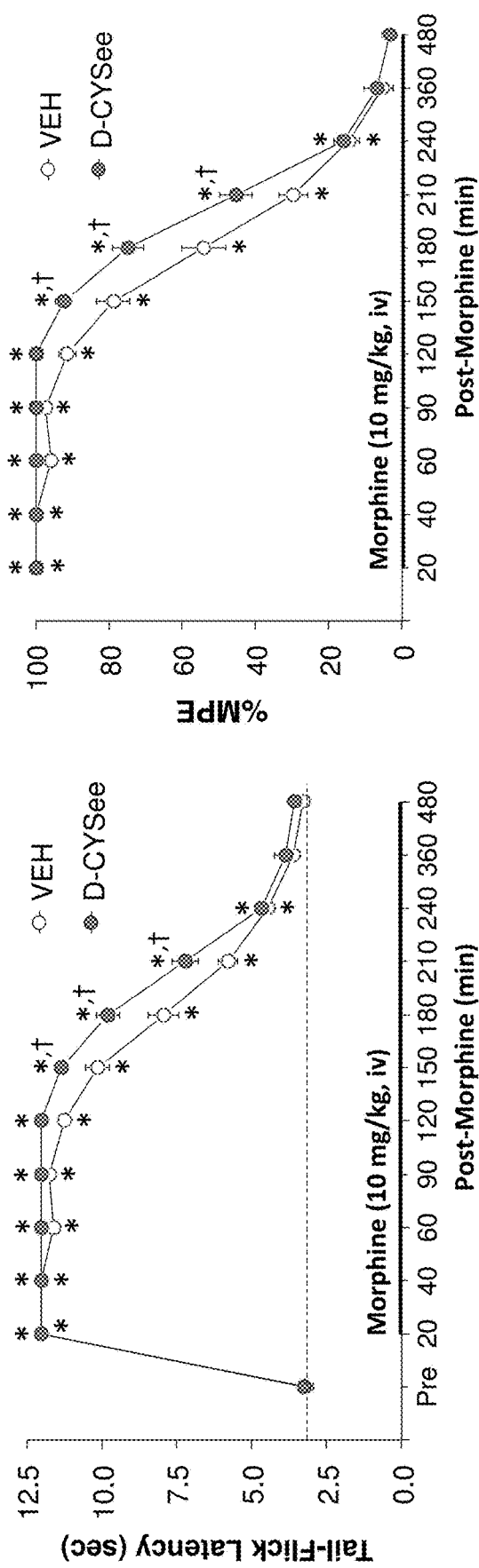
FIG. 17 illustrates plots showing that D-CYSee slightly augments 10 mg/kg morphine-induced analgesia.

FIG. 17 illustrates that D-CYSee slightly augments 10 mg/kg morphine-induced analgesia. Tail-Flick Latency (TFL)-time at which the rat will flick the tail upon exposure to a beam of radiant heat. D-CYSee (500 umol/kg, iv) or vehicle (saline, iv) were injected to Sprague-Dawley rats and after 15 min, TFL was determined (Pre value). Immediately afterwards, all rats received a bolus injection of morphine (10 mg/kg, iv) and TFL monitored at regular times thereafter. A cut-off latency of 12 sec was chosen to limit heat injury. Data are expressed as TFL (sec) and % MPE [% Maximum Possible Effect=((Morphine-induced TFL-pre-morphine TFL)/(Cut-off Latency-pre-drug latency))*100. Effects of D-CYSee (500 mol/kg, iv) on Tail-Flick latency in rats which had either received saline or morphine (10 mg/kg, iv). Data are presented as mean±SEM (n=9 rats per group). *$P<0.05$, difference from pre. †$P<0.05$, D-Cysteine ethylester (D-CYSee) versus vehicle.

FIG. 18 illustrates that D-CYSee slightly diminishes 5 mg/kg morphine-induced analgesia. Hot-Plate Latency (HPL)-time at which the rat will lift/lick a paw upon placement on a thermal plate of 55° C. in temperature. D-CYSee (500 umol/kg, iv) or vehicle (saline, iv) were injected to Sprague-Dawley rats and after 15 min, HPL was determined (Pre value). Immediately afterwards, all rats received a bolus injection of morphine (5 mg/kg, iv) and HPL monitored at regular times thereafter. A cut-off latency of 40 sec was chosen to limit heat injury. Data are expressed as HPL (sec) and % MPE [% Maximum Possible Effect=((Morphine-induced HPL-pre-morphine HPL)/(Cut-off Latency-pre-drug latency))*100. Effects of D-CYSee (500 mol/kg, iv) on Hot-Plate latency in rats which had either received saline or morphine (5 mg/kg, iv). Data are presented as mean±SEM (n=9 rats per group). *$P<0.05$, difference from pre. †$P<0.05$, D-Cysteine ethylester (D-CYSee) versus vehicle.

Figure 19:
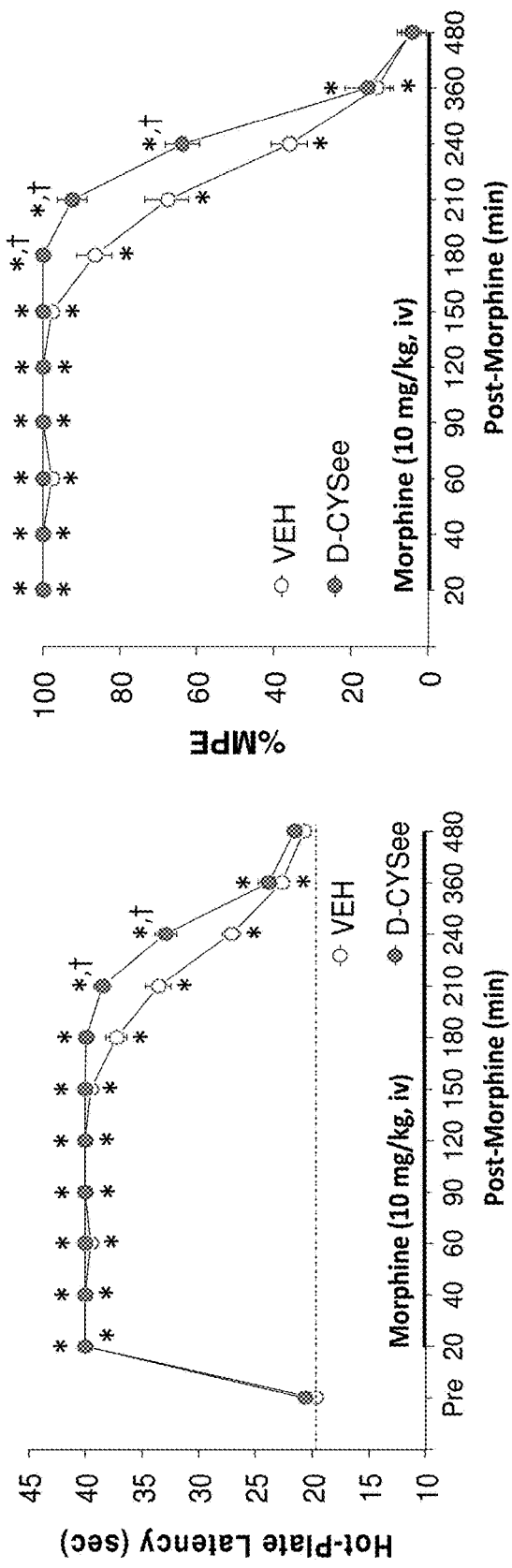
FIG. 19 illustrates plots showing that D-CYSee slightly augments 10 mg/kg morphine-induced analgesia.

FIG. 19 illustrates that D-CYSee slightly augments 10 mg/kg morphine-induced analgesia. Hot-Plate Latency (HPL)-time at which the rat will lift/lick a paw upon placement on a thermal plate of 55° C. in temperature. D-CYSee (500 umol/kg, iv) or vehicle (saline, iv) were injected to Sprague-Dawley rats and after 15 min, HPL was determined (Pre value). Immediately afterwards, all rats received a bolus injection of morphine (10 mg/kg, iv) and HPL monitored at regular times thereafter. A cut-off latency of 40 sec was chosen to limit heat injury. Data are expressed as HPL (sec) and % MPE [% Maximum Possible Effect=((Morphine-induced HPL-pre-morphine HPL)/(Cut-off Latency-pre-drug latency))*100. Effects of D-CYSee (500 mol/kg, iv) on Hot-Plate latency in rats which had either received saline or morphine (10 mg/kg, iv). Data are presented as mean±SEM (n=9 rats per group). *$P<0.05$, difference from pre. †$P<0.05$, D-Cysteine ethylester (D-CYSee) versus vehicle.

Figure 20:
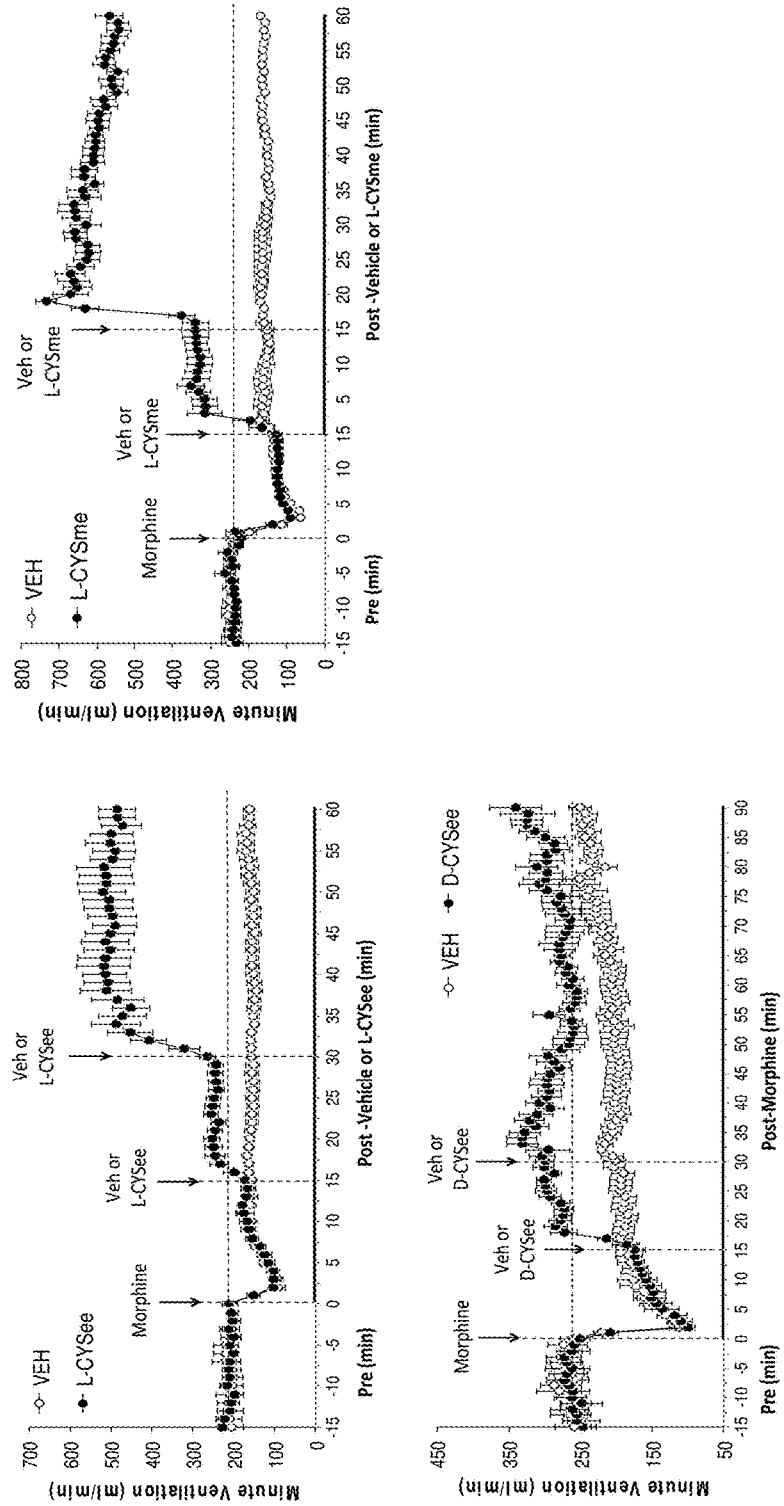
FIG. 20 illustrates plots showing that L-Cysteine ethylester (L-CYSee) and L-Cysteine methylester (L-CYSme) reverse the ventilatory effects of morphine with equal potency.

FIG. 20 illustrates that L-Cysteine ethylester (L-CYSee) and L-Cysteine methylester (L-CYSme) reverse the ventilatory effects of morphine with equal potency. Injection 2 of D-CYSee does not elicit the effects produced by injection 2 of L-CYSee and L-CYSme. D-CYSee does not feed into all pathways that L-CYSee and L-CYSme enter. Changes in minute ventilation elicited by acute bolus injects of vehicle (VEH), L-CYSee (2×500 mol/kg, iv). There were 9 rats in each group. Data are presented as mean±SEM.

FIG. 21 illustrates that L-Serine ethylester (L-SERee) does not reverse the ventilatory depressant effects of morphine. Ventilatory responses elicited by L-SERee (2×500 mol/kg, iv) in rats which had received morphine (10 mg/kg, iv). There were 9 rats in each group. Data are presented as mean±SEM.

FIG. 22 illustrates that N-acetyl-L-cysteine methylester (L-NACme) minimally affects the ventilatory effects of morphine. Substitutions on the amoni moiety of cysteine impair activity. Ventilatory responses elicited by L-NACme (2×500 mol/kg, iv) in rats which had received morphine (10 mg/kg, iv). There were 9 rats in each group. Data are presented as mean±SEM.

Figure 23:
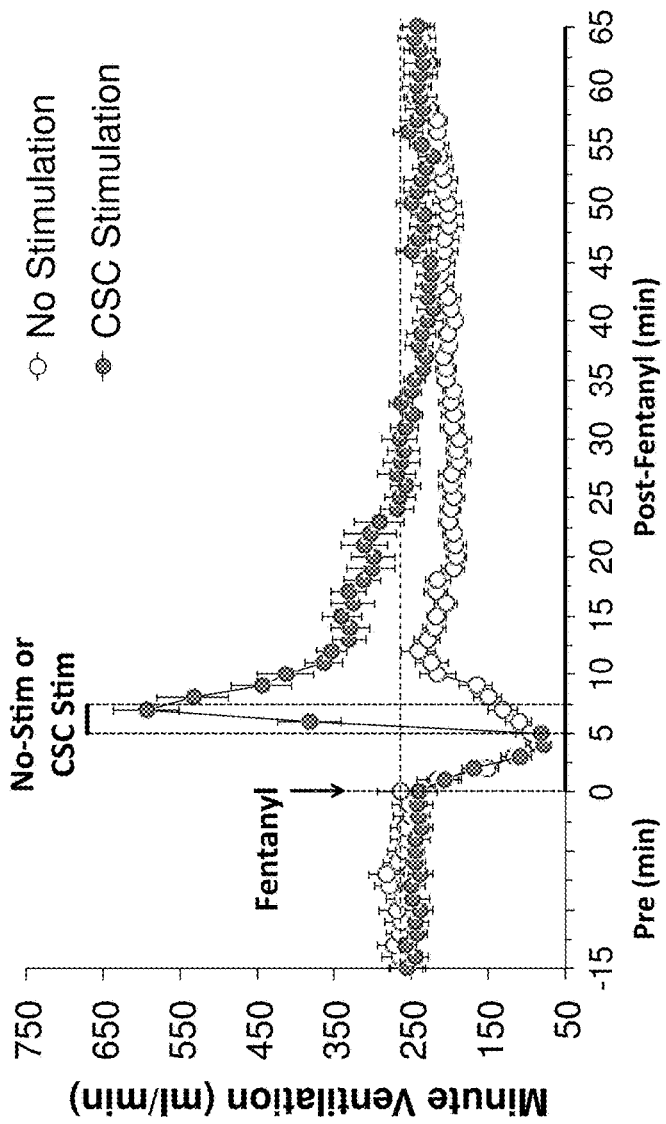
FIG. 23 illustrates a plot showing that bilateral electrical stimulation of the cervical sympathetic chain (CSC) reverses fentanyl-induced depression of minute ventilation in freely moving rats.

FIG. 23 illustrates that bilateral electrical stimulation of the cervical sympathetic chain (CSC) reverses fentanyl-induced depression of minute ventilation in freely moving rats. The left and right CDC provide preganglionic input to their ipsilateral superior cervical ganglion, which sends post-ganglionic projects to many sites in the periphery and central nervous system. Ventilatory responses elicited by bilateral CSC stimulation (5 Hz, 0.8 mA, 2 ms for 2.5 min) in rats which had received fentanyl (75 ug/kg, iv). There were 9 rats in each group. Data are presented as mean±SEM.

Figure 24:
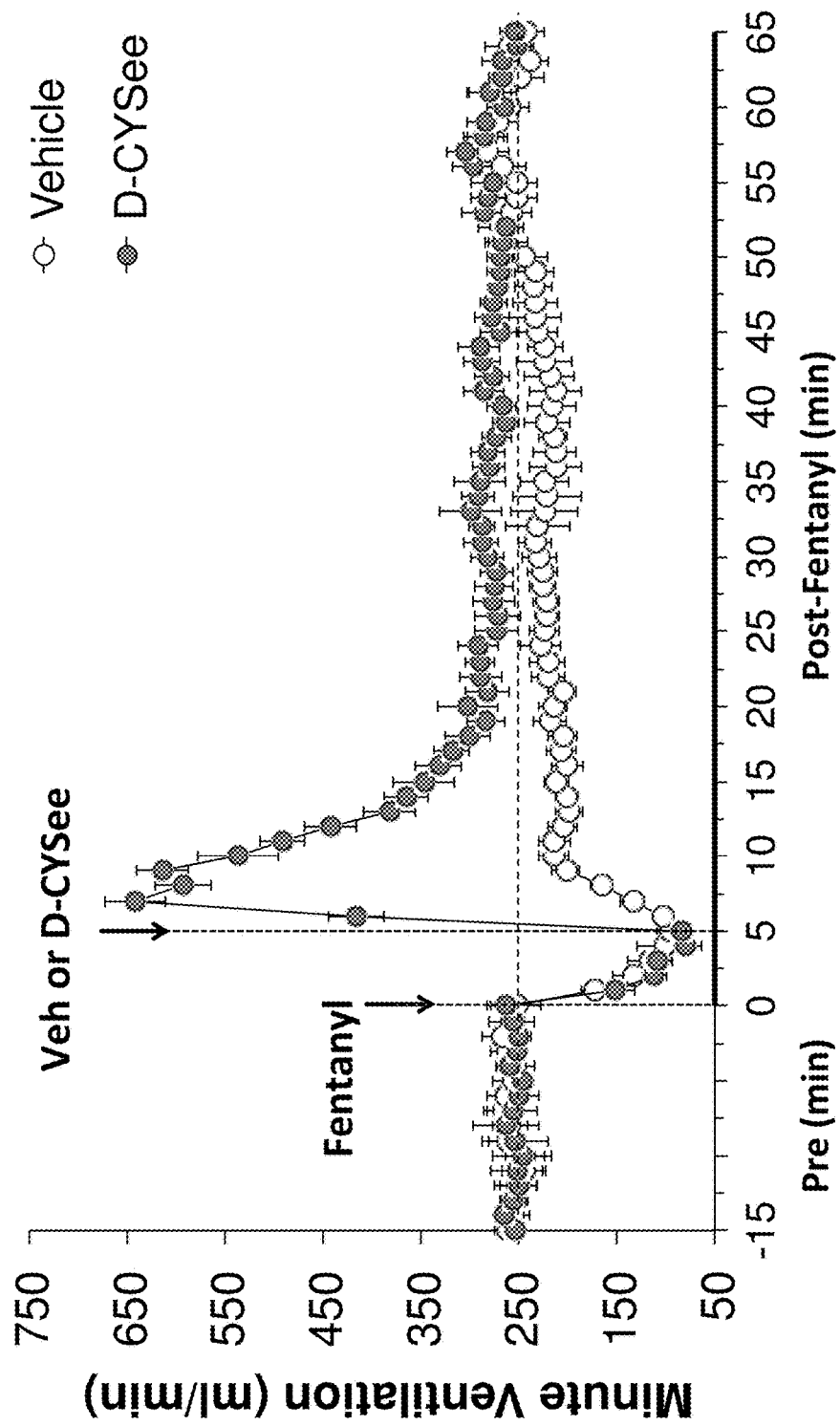
FIG. 24 illustrates a plot showing that D-cysteine ethylester (D-CYSee) reverses the ventilatory depressant effects of fentanyl in freely—moving rats.

FIG. 24 illustrates that D-cysteine ethylester (D-CYSee) reverses the ventilatory depressant effects of fentanyl in freely—moving rats. Ventilatory responses elicited by bolus injection of D-cysteine ethylester (D-CYSee, 500 mol/kg, iv) in rats which had received fentanyl (75 μg/kg, iv). There were 9 rats in each group. Data are presented as mean±SEM.

Figure 25:
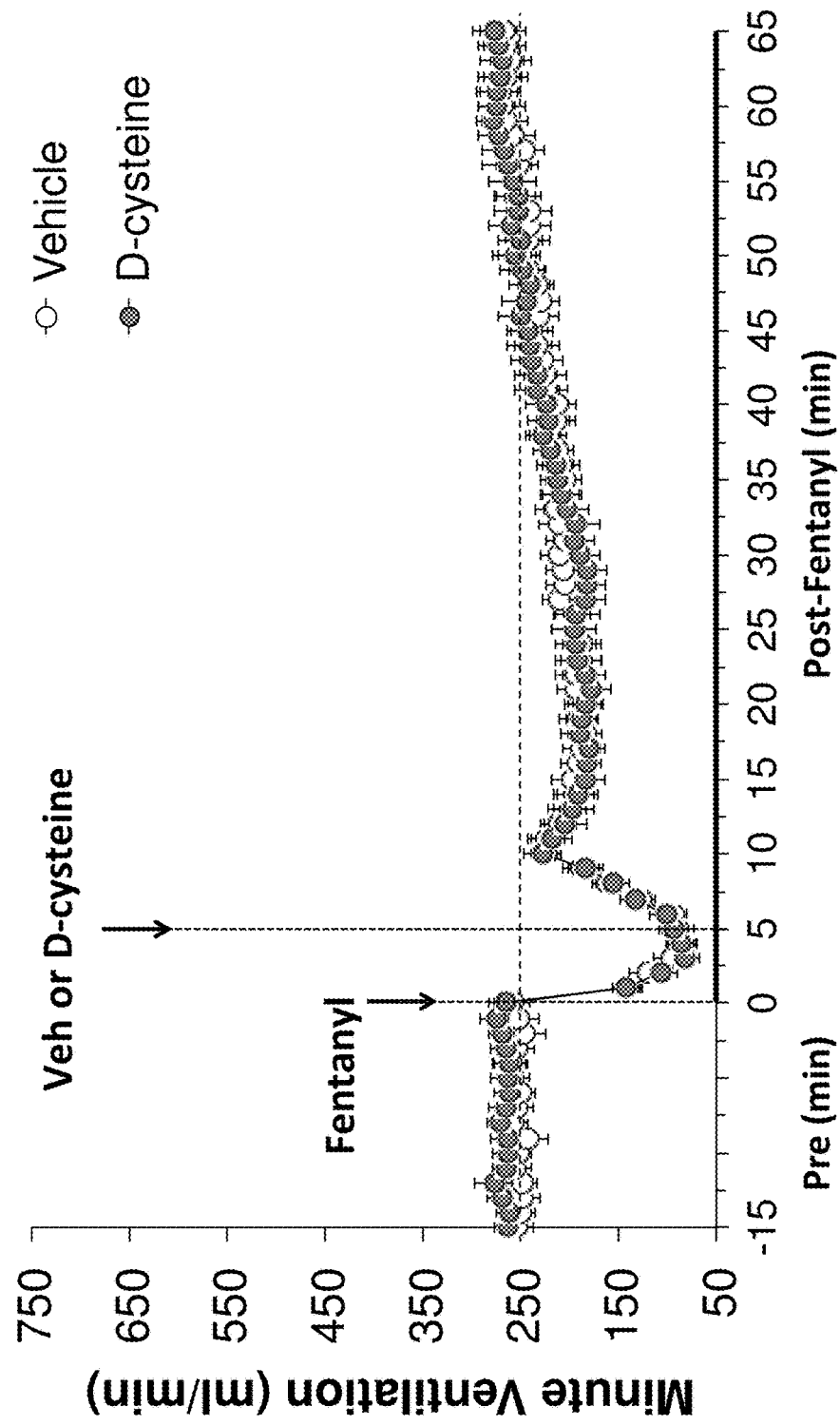
FIG. 25 illustrates a plot showing D-cysteine does not reverse the ventilatory depressant effects of fentanyl in freely-moving rats.

FIG. 25 illustrates D-cysteine does not reverse the ventilatory depressant effects of fentanyl in freely-moving rats. Ventilatory responses elicited by bolus injection of D-cysteine (500 μmol/kg, iv) in rats which had received fentanyl (75 μg/kg, iv). There were 9 rats in each group. Data are presented as mean±SEM.

More specifically, FIGS. 20 and 24 illustrates that the highly cell permeable ethyl ester forms of L-cysteine and D-cysteine, namely D-cysteine ethyl ester (D-CYSee) and L-cysteine ethyl ester (L-CYSee) elicited dramatic reversal of opiate (e.g., morphine, fentanyl)-induced respiratory depression.

It was further shown that L-CYSee has deleterious effects not shared by D-CYSee, most likely because L-CYSee feeds into metabolic pathways that D-CYSee cannot. The findings that certain structural modifications to L- or D-CYSee eliminate activity whereas L-serine (identical to cysteine with oxygen atom rather than sulfur atom) is inactive indicate that the CYSee moiety-sulfur atom is essential for activity against morphine ventilatory depression.

The present findings illustrate that D-CYSee reverses the deleterious effects of morphine on ventilation and arterial blood-gas chemistry in freely-moving rats without compromising the analgesic effects of the opioid.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, we claim:

1. A method of stimulating ventilatory and/or respiratory drive in a subject in need thereof, the method comprising:
administering to the subject a therapeutically effective amount of a composition comprising a D-cysteine alkyl ester, adduct thereof, or pharmaceutically acceptable salt, tautomer, or solvate thereof.

2. The method of claim 1, the D-cysteine alkyl ester comprising a compound having the structure of the formula:

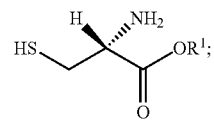

where $R^1$ is an unsubstituted or substituted lower alkyl ($C_1$-$C_6$ alkyl) or pharmaceutically acceptable salts, tautomers, or solvates thereof.

3. The method of claim 1, wherein the D-cysteine alkyl ester comprises a D-cysteine ethyl ester, adduct thereof, or pharmaceutically acceptable salt, tautomer, or solvate thereof.

4. The method of claim 1, wherein the adduct of the D-cysteine alkyl ester comprises at least one of an albumin adduct, a glucose adduct, an L-cysteine adduct, an L-glutathione adduct, and an S-nitroso adduct.

5. The method of claim 1, wherein the therapeutically effective amount is an amount effective to stimulate the ventilatory and/or respiratory drive of the subject, increase tidal volume, increase respiratory frequency, increase minute ventilation, increase peak inspiratory flow, increase inspiratory drive, and/or increase Alveolar-arterial (A-a) gradient.

6. The method of claim 1, wherein the subject has or is at increased risk of respiratory depression, sleep apnea, apnea of prematurity, obesity-hyperventilation syndrome, primary alveolar hypoventilation syndrome, dyspnea, altitude sickness, hypoxia, hypercapnia, cystic fibrosis, and chronic obstructive pulmonary disease (COPD).

7. The method of claim 6, wherein the narcotic is an opioid.

8. The method of claim 1, wherein the subject has or is at increase risk of respiratory depression, wherein the respiratory depression is caused by anesthetic, a sedative, anxiolytic agent, a hypnotic agent, alcohol, and/or a narcotic.

9. The method of claim 8, wherein the opioid is fentanyl or morphine.

10. The method of claim 1, further comprising administering at least one additional composition selected from the group consisting of an opioid, doxapram and enantiomers thereof, acetazolamide, almitrine, theophylline, caffeine, methylprogesterone and related compounds, sedatives that decrease arousal threshold in sleep disordered breathing patients, sodium oxybate, benzodiazepine receptor agonists, orexin antagonists, tricyclic antidepressants, serotonergic modulators, adenosine and adenosine receptor and nucleoside transporter modulators, cannabinoids, orexins, melatonin agonists, ampakines, and combinations thereof.

11. A method of reversing at least one of opioid induced respiratory depression in a subject in need thereof, the method comprising:
administering to the subject a therapeutically effective amount of a composition comprising D-cysteine alkyl ester, adduct thereof, or pharmaceutically acceptable salt, tautomer, or solvate thereof.

12. The method of claim 11, the D-cysteine alkyl ester comprising a compound having the structure of formula:

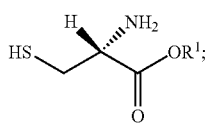

where $R^1$ is an unsubstituted or substituted lower alkyl ($C_1$-$C_6$ alkyl) or pharmaceutically acceptable salt, tautomer, or solvate thereof.

13. The method of claim 11, wherein the D-cysteine alkyl ester comprises a D-cysteine ethyl ester, adduct thereof, or pharmaceutically acceptable salt, tautomer, or solvate thereof.

14. The method of claim 11, wherein the adduct thereof of the D-cysteine alkyl ester comprises at least one of an albumin adduct, a glucose adduct, an L-cysteine adduct, an L-glutathione adduct, and an S-nitroso adduct.

15. The method of claim 11, wherein the therapeutically effective amount is an amount effective to stimulate the ventilatory and/or respiratory drive of the subject, increase tidal volume, increase respiratory frequency, increase minute ventilation, increase peak inspiratory flow, increase inspiratory drive, and/or increase Alveolar-arterial (A-a) gradient.

16. The method of claim 11, wherein the D-cysteine alkyl ester, adduct thereof, or pharmaceutically acceptable salt thereof is administered to the subject at an amount effective to decreases the deleterious effects of the opioid on breathing, chest-wall rigidity, ventilation-perfusion within the lungs, and arterial blood-gas chemistry without compromising the analgesic effects of the opioid in the subject.

17. The method of claim 11, wherein the opioid is fentanyl or morphine.

18. The method of 11, wherein the composition is administered to the subject systemically.

19. A composition comprising:
an opioid capable of inducing respiratory depression in a subject and an amount of a D-cysteine alkyl ester, adduct thereof, or pharmaceutically acceptable salt, tautomer, or solvate thereof effective to prevent the opioid induced respiratory depression when the composition is administered to the subject.

20. The composition of claim 19, wherein the D-cysteine alkyl ester comprising the formula:

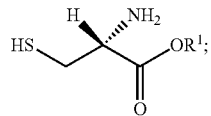

where $R^1$ is an unsubstituted or substituted lower alkyl ($C_1$-$C_6$ alkyl) or pharmaceutically acceptable salt, tautomer, or solvate thereof.

\* \* \* \* \*